United States Patent
Penake et al.

(10) Patent No.: US 11,654,124 B2
(45) Date of Patent: *May 23, 2023

(54) STABILIZED FORMULATIONS OF 4-AMINO-3-SUBSTITUTED BUTANOIC ACID DERIVATIVES

(71) Applicant: AMNEAL PHARMACEUTICALS LLC, Bridgewater, NJ (US)

(72) Inventors: David Penake, Atlanta, GA (US); Sharon Hamm, Odessa, FL (US); Leonard O'Mahony, Westmeath (IE); John Devane, Dublin (IE); Wolfgang Mohr, Freiburg (DE); Manuel Weinheimer, Neustadt an der Weinstrasse (DE)

(73) Assignee: AMNEAL PHARMACEUTICALS LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/630,297

(22) PCT Filed: May 28, 2020

(86) PCT No.: PCT/US2020/034840
§ 371 (c)(1),
(2) Date: Jan. 26, 2022

(87) PCT Pub. No.: WO2021/021277
PCT Pub. Date: Feb. 4, 2021

(65) Prior Publication Data
US 2022/0265588 A1    Aug. 25, 2022

Related U.S. Application Data

(63) Continuation-in-part of application No. 16/524,664, filed on Jul. 29, 2019, now Pat. No. 10,792,262.

(51) Int. Cl.
*A61K 31/197* (2006.01)
*A61K 9/20* (2006.01)
*A61K 9/16* (2006.01)

(52) U.S. Cl.
CPC .......... *A61K 31/197* (2013.01); *A61K 9/1611* (2013.01); *A61K 9/1623* (2013.01); *A61K 9/1635* (2013.01); *A61K 9/1664* (2013.01); *A61K 9/2027* (2013.01)

(58) Field of Classification Search
CPC .............................. A61K 31/197; A61K 9/2027
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,557,925 A | 12/1985 | Lindahl et al. |
| 4,863,742 A | 9/1989 | Panoz et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 7,309,719 B1 | 12/2007 | Aomatsu |
| 9,504,658 B2 | 11/2016 | Miller et al. |
| 10,792,262 B1 * | 10/2020 | Penake ............... A61K 9/1635 |
| 2005/0106239 A1 | 5/2005 | Tenengauzer et al. |
| 2006/0039968 A1 | 2/2006 | Manikandan et al. |
| 2010/0216887 A1 | 8/2010 | Foster et al. |
| 2011/0091542 A1 | 4/2011 | Navon |
| 2011/0200671 A1 | 8/2011 | Dharmadhikari et al. |
| 2016/0120809 A1 | 5/2016 | Djordjevic |

FOREIGN PATENT DOCUMENTS

| | | |
|---|---|---|
| EP | 2 072 057 | 6/2009 |
| WO | 2008/101554 A1 | 8/2008 |
| WO | 2014/100403 A1 | 6/2014 |
| WO | 2016/087952 A1 | 6/2016 |
| WO | 2017/116031 A1 | 7/2017 |

OTHER PUBLICATIONS

Abdelkader, H., Youssef Abdalla, O. & Salem, H. Formulation of Controlled-Release Baclofen Matrix Tablets II: Influence of Some Hydrophobic Excipients on the Release Rate and In Vitro Evaluation. AAPS PharmSciTech 9, 675-683 (2008). (Year: 2008).*

Moustafine, R. I., et al. "Eudragit E PO as a complementary material for designing oral drug delivery systems with controlled release properties: comparative evaluation of new interpolyelectrolyte complexes with countercharged eudragit L100 copolymers." Molecular pharmaceutics 10.7 (2013): 2630-2641. (Year: 2013).*

Shanmugam S. Granulation techniques and technologies: recent progresses. Bioimpacts. 2015;5(1):55-63. (Year: 2015).*

Evonik, Eduragit setting benchmarks in oral solid dosage forms since 1954, obtained online at: https://web.archive.org/web/20170119111029/https://healthcare.evonik.com/sites/lists/nc/documentshc/evonik-eudragit_brochure.pdf, downloaded on Jan. 23, 2023. (Year: 2017).*

Mylan, Amlopidine besylate/atorvastatin calcium tablets. (Year: 2016).*

(Continued)

*Primary Examiner* — Abigail Vanhorn
(74) *Attorney, Agent, or Firm* — Greenblum & Bernstein, P.L.C.

(57) ABSTRACT

Pharmaceutical compositions including an active ingredient and a stabilizer, as well as methods of manufacture of the compositions, and methods of their use. The composition may include the active ingredient dispersed throughout a matrix of the stabilizer. In some embodiments, the active ingredient and the stabilizer are intimately mixed in a matrix formulation. In some embodiments, the active ingredient is selected from 4 amino-3-(4-chlorophenyl)butanoic acid) ("baclofen") and its pharmaceutically acceptable salts.

13 Claims, 18 Drawing Sheets

(56) References Cited

OTHER PUBLICATIONS

Fine-Shamir, Noa, and Arik Dahan. "Methacrylate-copolymer Eudragit EPO as a solubility-enabling excipient for anionic drugs: investigation of drug solubility, intestinal permeability, and their interplay." Molecular Pharmaceutics 16.7 (2019): 2884-2891. (Year: 2019).*

Janardhan et al., International Journal of Pharmaceutical Sciences and Nanotechnology, 2(4), pp. 733-738, 2010.

ISR issued in International Patent Application No. PCT/US2020/034840, Aug. 14, 2020.

IPRP issued in International Patent Application No. PCT/US2020/034840, Feb. 1, 2022.

EESR issued in EP Patent Application No. 20847638.2, dated Apr. 5, 2023 (received Mar. 31, 2023).

* cited by examiner

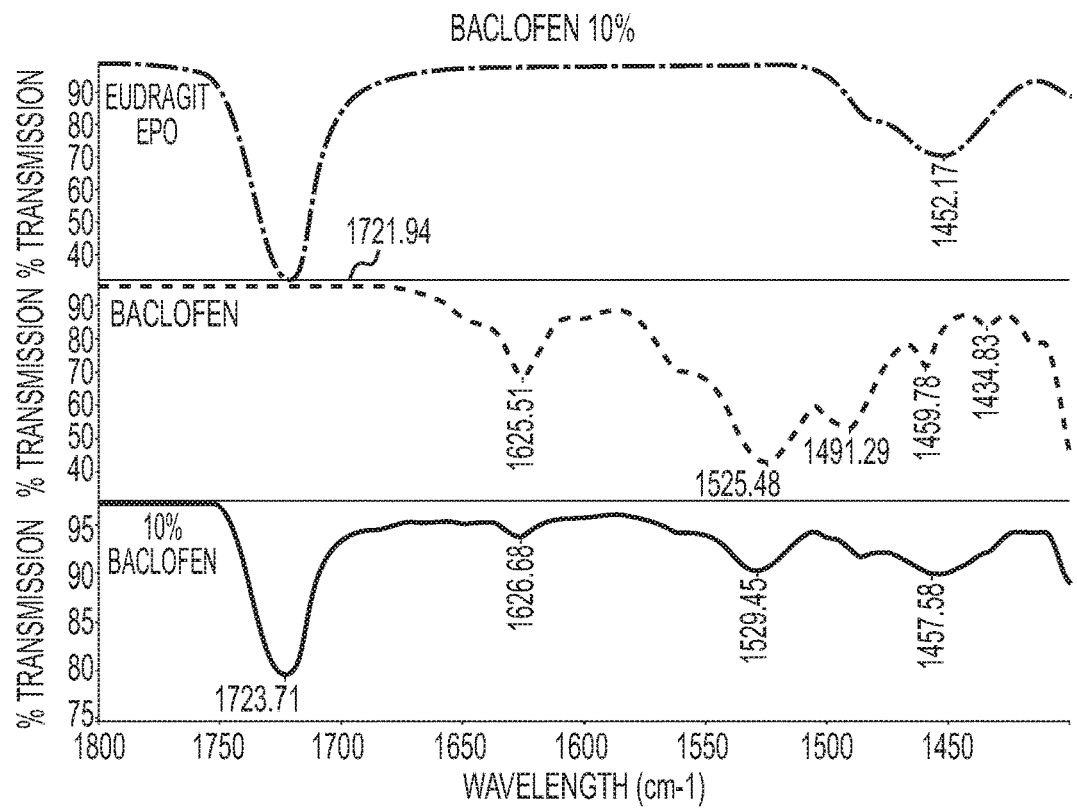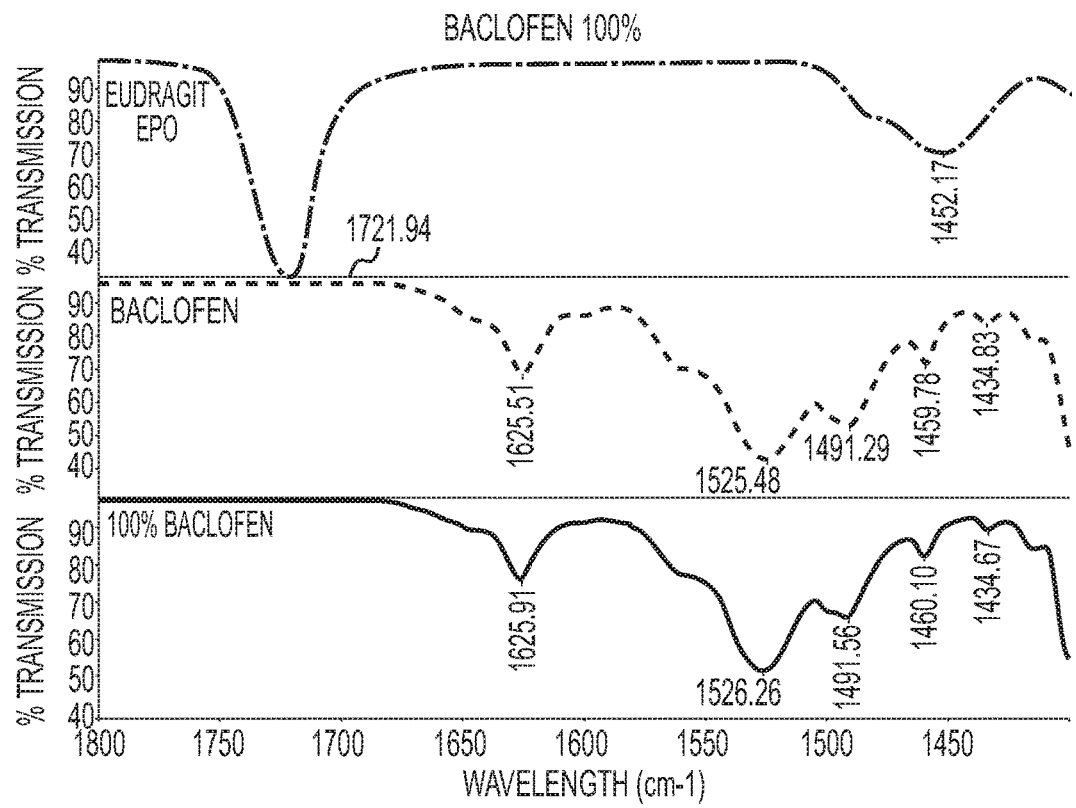
FIG. 15

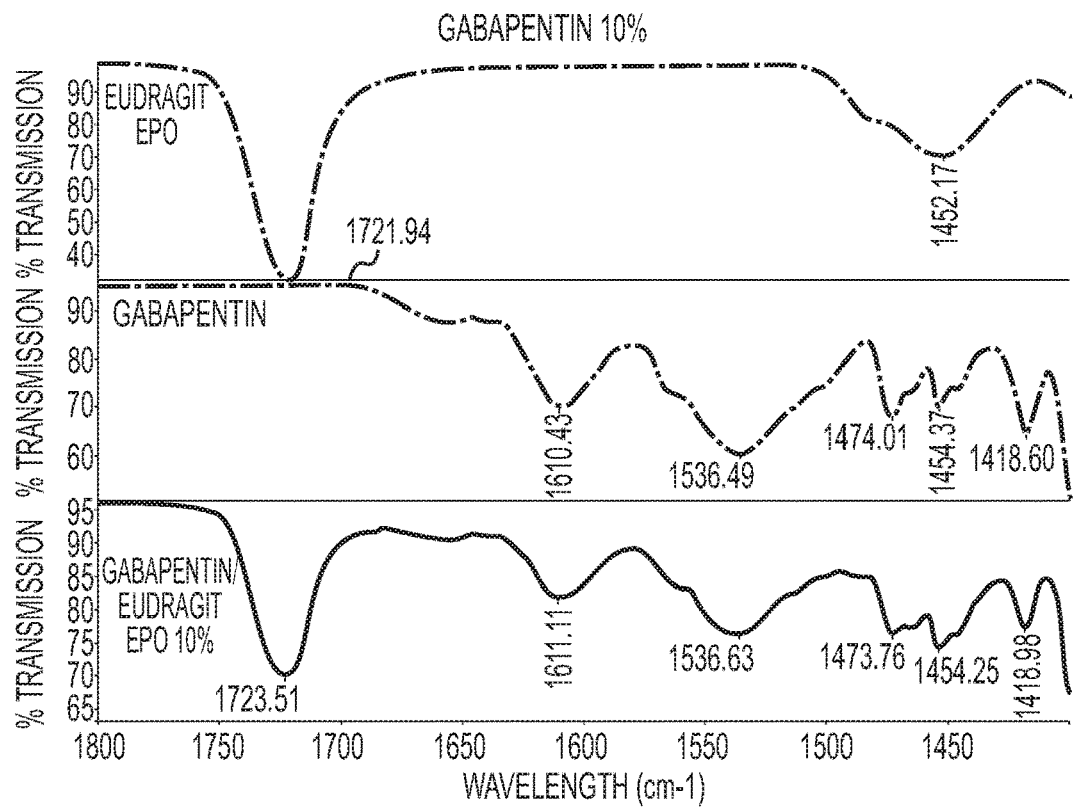
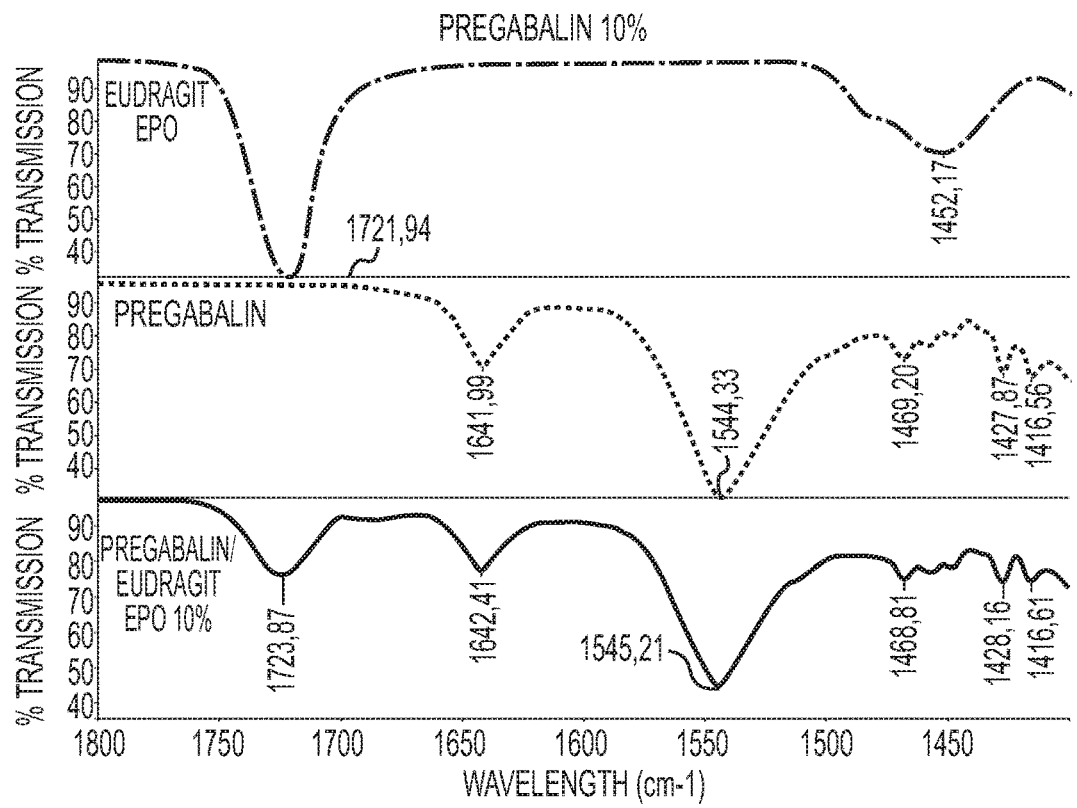
FIG. 16

STABILIZED FORMULATIONS OF 4-AMINO-3-SUBSTITUTED BUTANOIC ACID DERIVATIVES

CROSS-REFERENCE TO RELATED APPLICATIONS

This application claims priority from U.S. application Ser. No. 16/524,664, filed Jul. 29, 2019, which is hereby incorporated by reference in its entirety.

FIELD

This application relates to, among other things, stabilized formulations of 4-amino-3-substituted butanoic acid derivatives in particular, and more generally, to lactam-forming drugs.

BACKGROUND

4-Amino-3-substituted-butanoic acid derivatives, such as baclofen, gabapentin, and pregabalin, are susceptible to intramolecular autocondensation between amino and carboxyl groups that forms lactams. The autocondensation reaction rate increases as storage temperatures are elevated. Also, baclofen, pregabalin, and gabapentin are dry powders that can have poor compression-moldability and flow. However, many of the auxiliaries conventionally used to improve compression-moldability and/or flow also increase autocondensation reaction rates in formulations of 4-amino-3-substituted butanoic acid derivatives. Consequently, pharmaceutical dosage forms such as capsules, tablets, granules, and (semi)-liquid preparations of 4-amino-3-substituted butanoic acid derivatives can have their shelf lives limited due to stability issues.

The solution to a shelf-stability problem can often be found by studying the cause of the instability. For example, drugs that are sensitive to acid can often be stabilized by formulating with bases, and base-sensitive drugs can be stabilized by formulating with acids. Drugs susceptible to free radical oxidation can often be stabilized with antioxidants. Recognizing that 4-amino-3-substituted-butanoic acid derivatives, such as baclofen, gabapentin, and pregabalin, are susceptible to intramolecular autocondensation between amino and carboxyl groups that form lactams, the inventors of U.S. Pat. No. 7,309,719 proposed adding an amino acid as a stabilizer to 4-amino-3-substituted-butanoic acid derivatives to reduce lactam formation and thus improve storage stability.

SUMMARY

However, in some circumstances, the solution to a problem is not a result of deliberate design, but is a matter of serendipity. Such is the case here, where the present inventors surprisingly discovered that well-known release rate-controlling polymers comprising a methacrylate component provide a profound and unexpected ability to stabilize certain 4-amino-3-substituted-butanoic acid derivatives.

The invention provides pharmaceutical compositions, comprising: an active ingredient; and a stabilizer. The composition may include the active ingredient dispersed throughout a matrix of the stabilizer. In some embodiments, the active ingredient and the stabilizer are intimately mixed in a matrix formulation. In some embodiments, the active ingredient is selected from 4 amino-3-(4-chlorophenyl)butanoic acid) ("baclofen") and its pharmaceutically acceptable salts.

In certain compositions, a weight ratio of the stabilizer to the active ingredient may be from 1.5:1 to 10:1, or from 1.8:1 to 7.2:1. In some embodiments, the composition will further comprising an excipient. Example of excipients include one or more glidants, lubricants, fillers, sweeteners, taste-masking agents, disintegrants, saliva-forming agents, binding agents, or flavorings. Specific excipients include xylitol, mannitol, saccharin sodium, hypromellose, crospovidone, calcium stearate, colloidal silicon dioxide, talc, and flavoring.

In some embodiments of the composition, the stabilizer is a methyl methacrylate copolymer, methacrylic acid copolymer, ammonioalkyl methacrylate copolymer, or amino alkyl methacrylate copolymer. In certain embodiments, the stabilizer is poly(butylmethacrylate-co-(2-dimethylaminoethyl) methacrylate-co-methyl methacrylate. The composition may further comprise one or more excipients selected from xylitol, calcium stearate, colloidal silicon dioxide, talc, and flavoring. The pharmaceutical composition may take the form of a solid dosage form.

The invention further provides methods of making the pharmaceutical composition comprising intimately mixing together the active ingredient and stabilizer. In embodiments, the intimately mixing may comprise at least one of wet granulation and dry granulation. In embodiments, the intimately mixing comprises dry blending. In some embodiments, the methods of making may further comprise dry compacting or slugging to form a solid dosage form. In embodiments, the methods may further comprise coating a solid dosage form. In certain embodiments, the method of making comprises wet granulation, wherein the wet granulation comprises dry blending the active ingredient and stabilizer, then adding a solvent, and granulating the mixture.

The invention further provides methods of reducing lactam formation in a baclofen formulation, the method comprising intimately mixing together baclofen or a pharmaceutically acceptable salt thereof and a stabilizer. In some embodiments, the baclofen is micronized. In some embodiments, the method comprises milling the baclofen to reduce its particle size before intimately mixing with the stabilizer.

The invention provides methods of increasing the shelf life of a solid baclofen formulation, the method comprising: reducing formation of 4-CPP in a baclofen formulation by intimately mixing together baclofen or a pharmaceutically acceptable salt thereof and a stabilizer to form a solid baclofen formulation. The methods may result in an amount of 4-CPP in the solid baclofen formulation that increases by no more than 0.2% after six months of stability testing at 40° C., 75% relative humidity. In some embodiments, the amount of 4-CPP in the solid baclofen formulation increases by no more than 0.1% after six months of stability testing at 40° C., 75% relative humidity.

Then invention further provides methods of treating spasticity, comprising administering to a patient in need thereof an effective amount of the compositions of the invention.

Additional features and advantages of the present disclosure will be set forth in part in the description that follows, and in part will be apparent from the description, or may be learned by practice of the present disclosure. The objectives and other advantages of the present disclosure will be realized and attained by means of the elements and combinations particularly pointed out in the description and claims.

The foregoing general description and the following detailed description are exemplary and explanatory only to provide a further explanation of the present disclosure and are not restrictive of the scope of the subject matter encompassed by the claims.

BRIEF DESCRIPTION OF THE DRAWINGS

FIG. 15 shows IR spectra of a 90:10 E PO/baclofen mixture and 100% baclofen.

FIG. 16 shows IR spectra of E PO/gabapentin and E PO/pregabalin mixtures.

DETAILED DESCRIPTION

Figure 1:
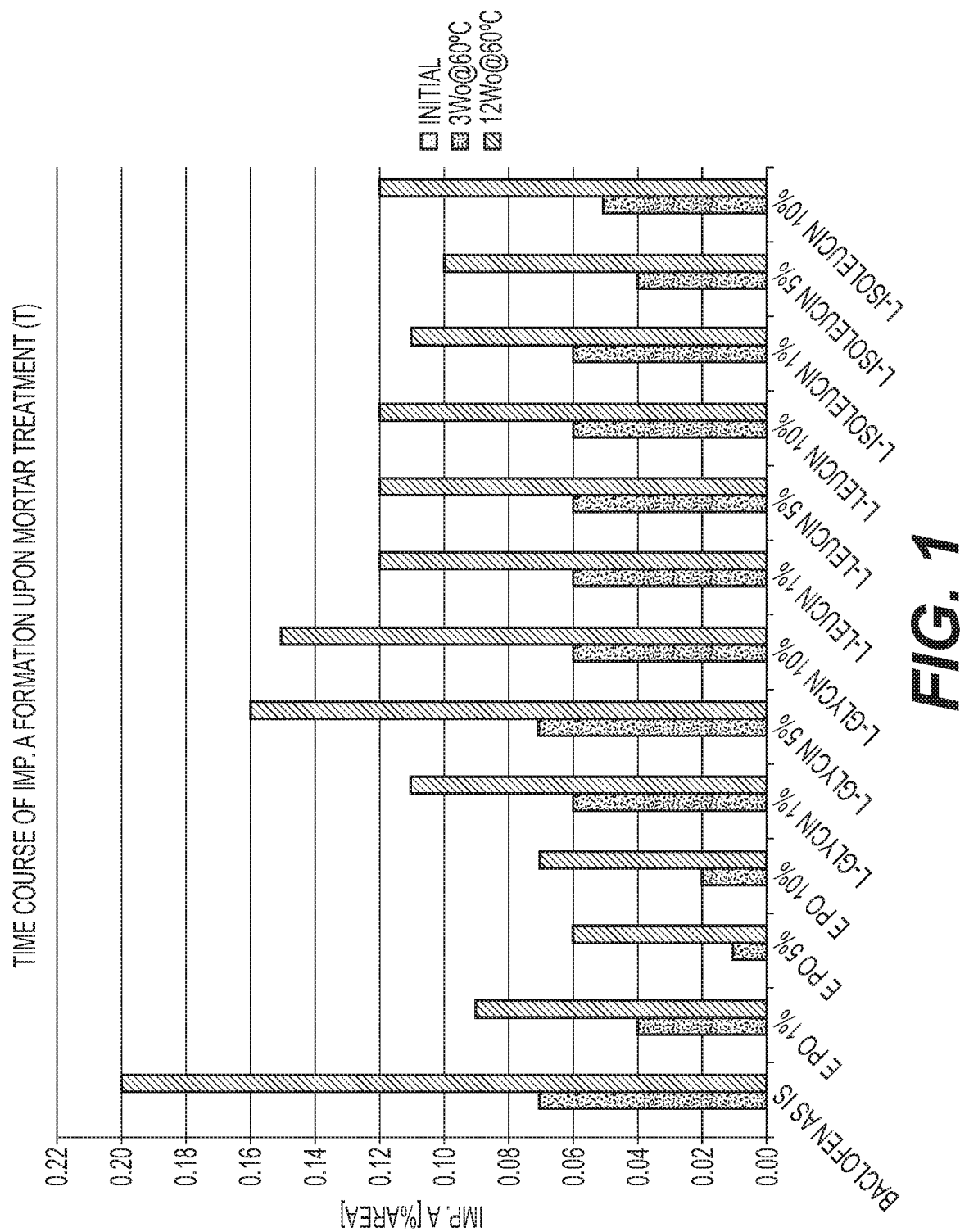
FIG. 1 is a graph of the formation of 4-CPP at different storage times for various baclofen mortar treatment formulations with different E PO levels compared with amino acids.
Figure 2:
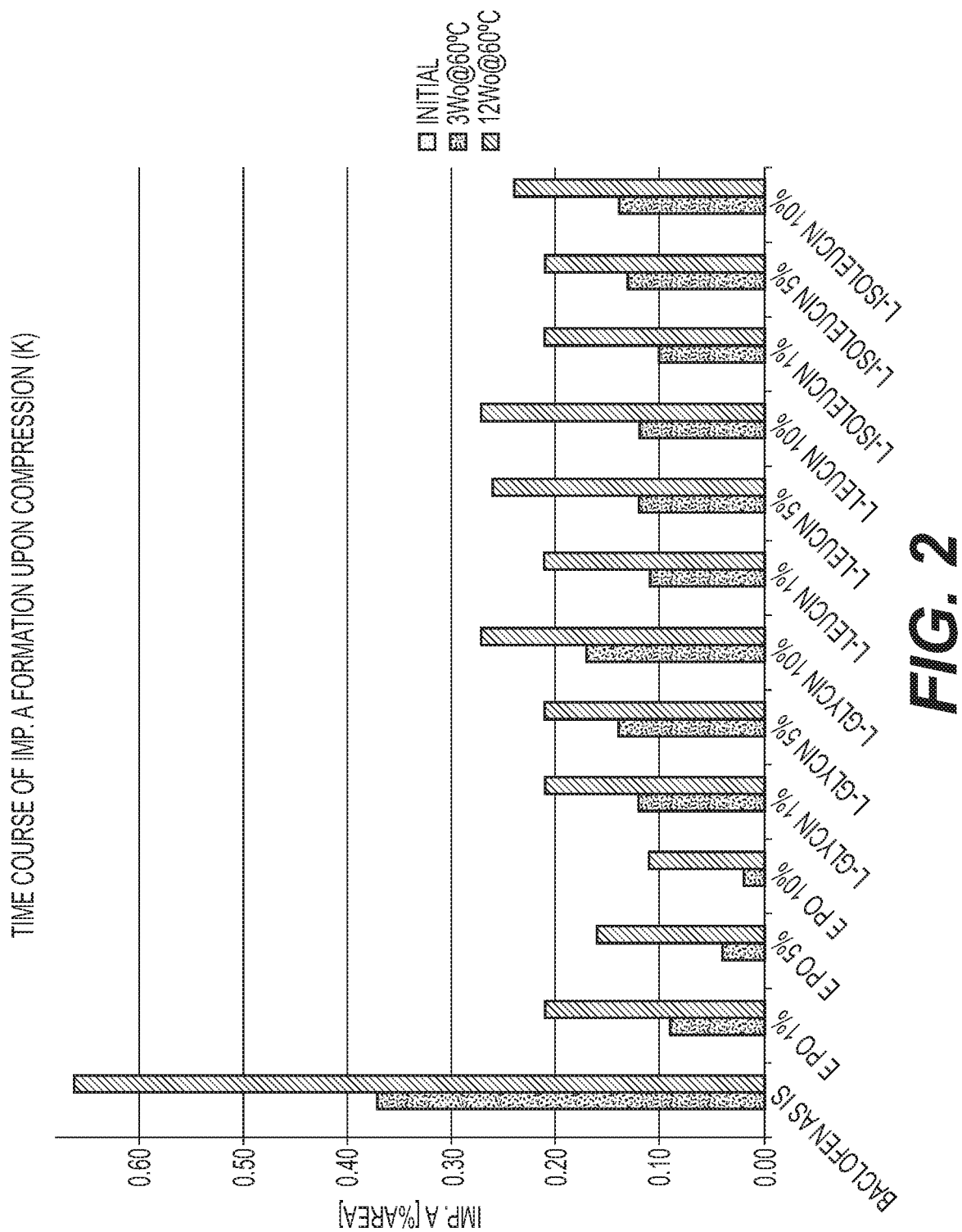
FIG. 2 is a graph of the formation of 4-CPP at different storage times for various baclofen compression formulations with different E PO levels compared with amino acids.
Figure 3:
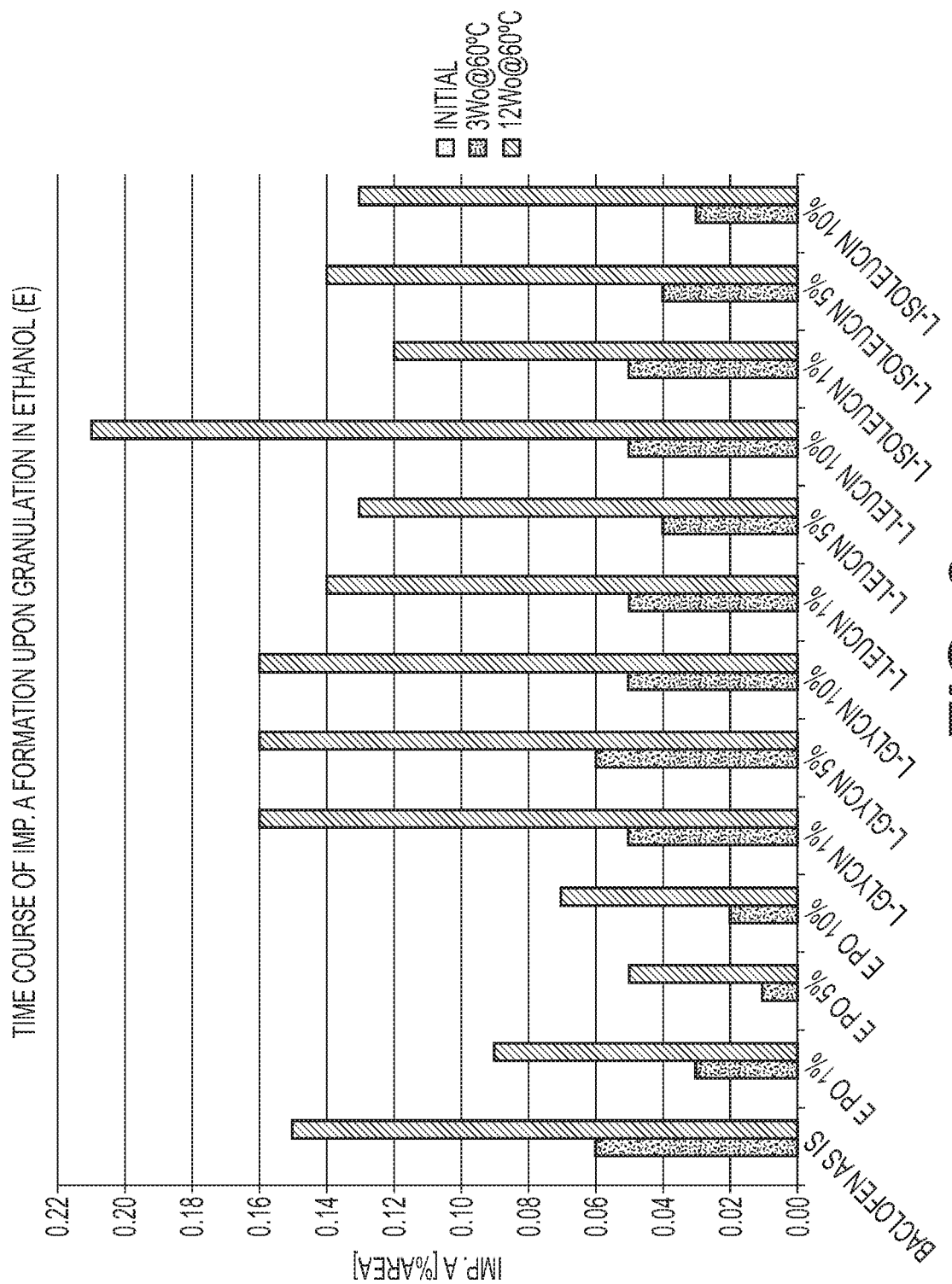
FIG. 3 is a graph of the formation of 4-CPP at different storage times for various baclofen ethanol granulation formulations with different E PO levels compared with amino acids.
Figure 4:
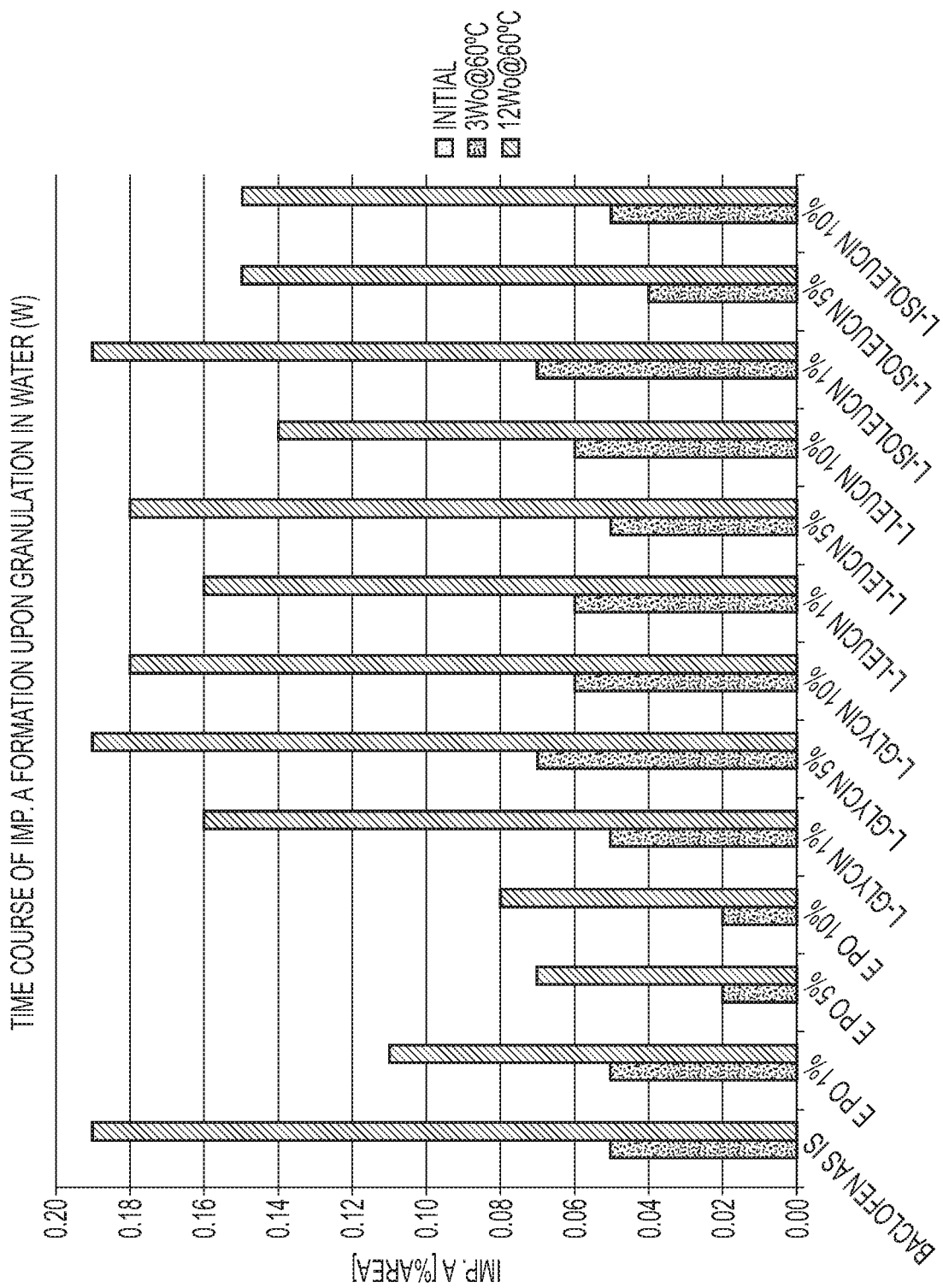
FIG. 4 is a graph of the formation of 4-CPP at different storage times for various baclofen water granulation formulations with different E PO levels compared with amino acids.
Figure 5:
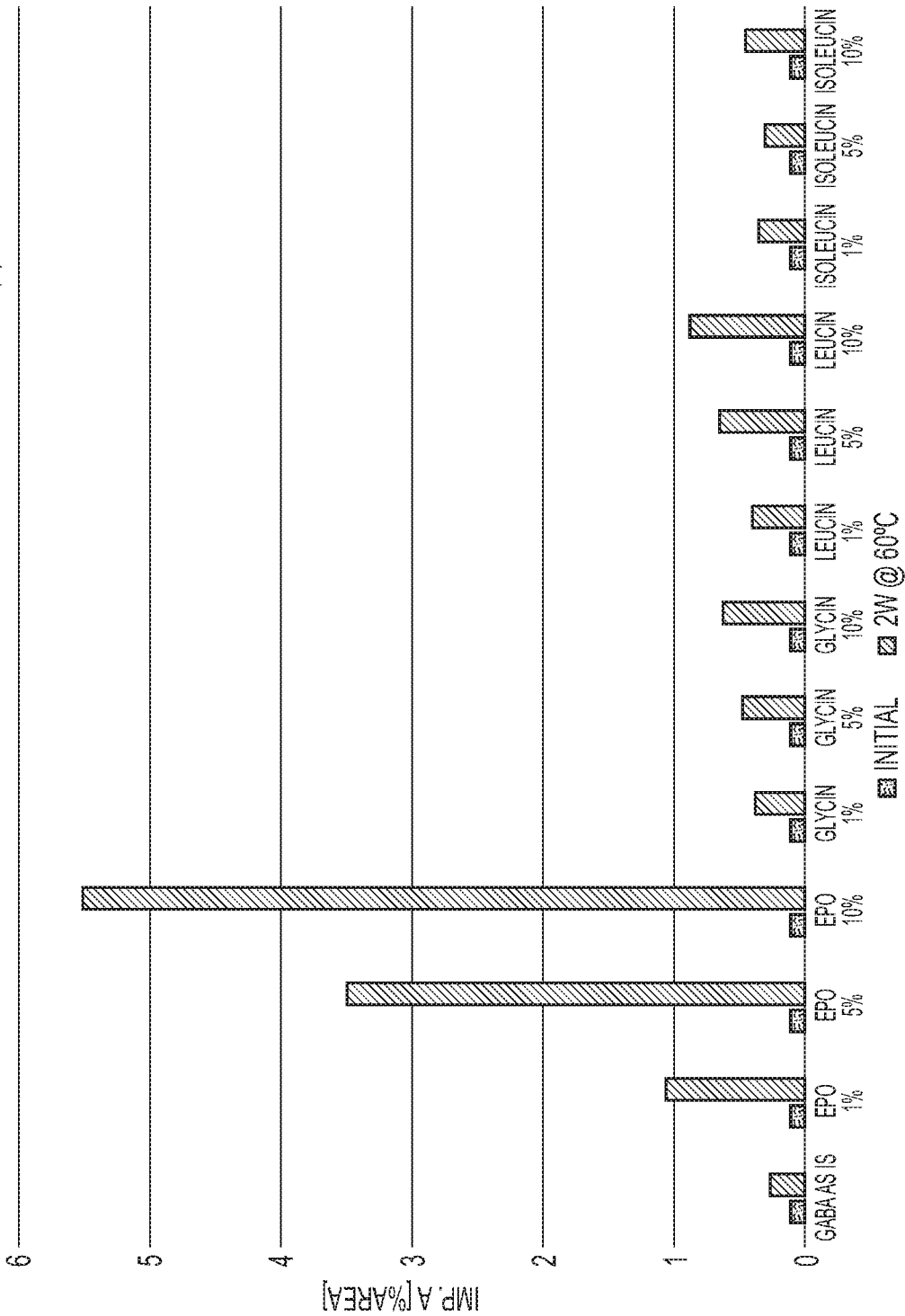
FIG. 5 is a graph of the formation of Impurity A at different storage times for various gabapentin mortar treatment formulations with different EPO levels compared with amino acids.
Figure 6:
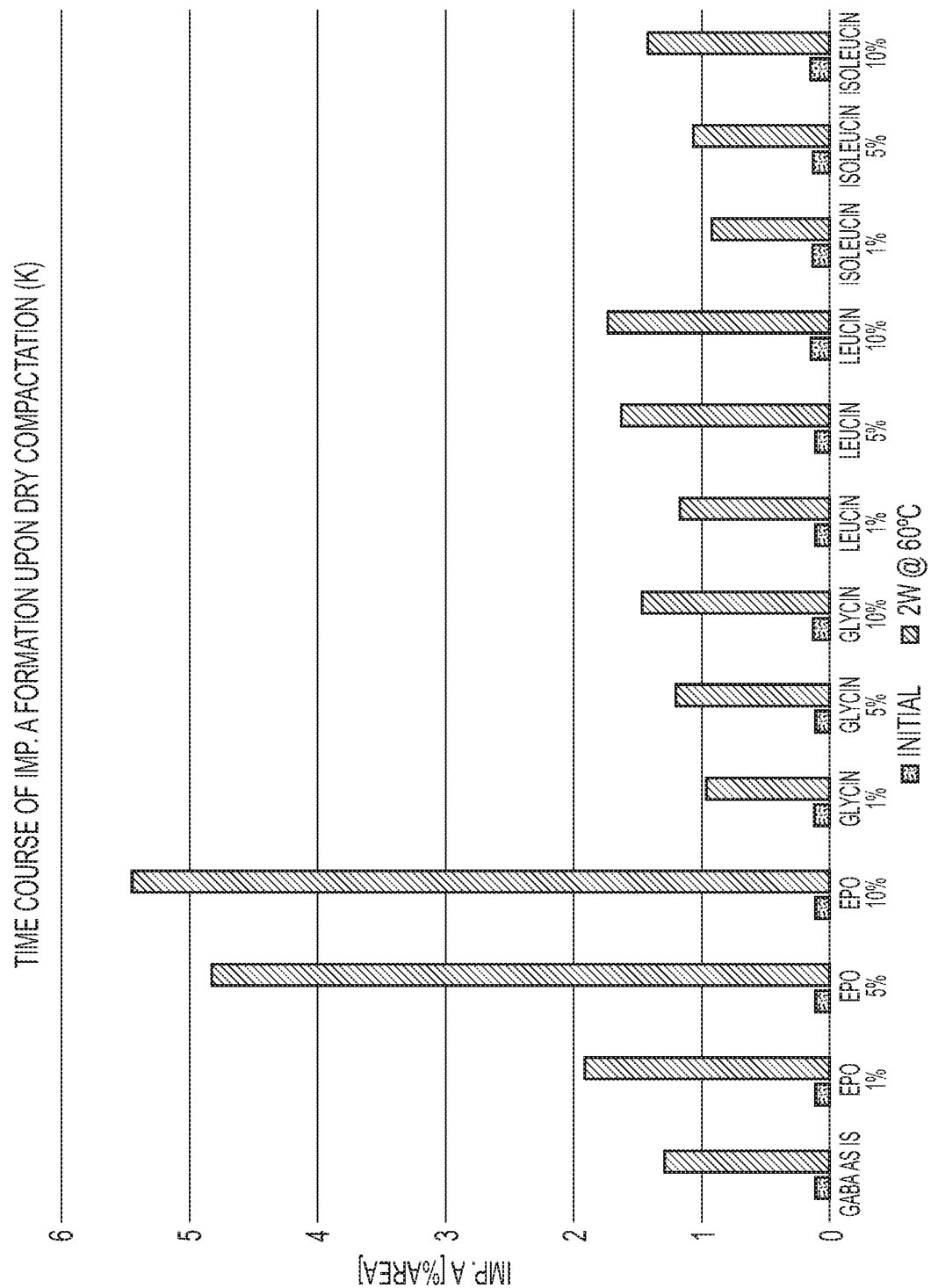
FIG. 6 is a graph of the formation of Impurity A at different storage times for various gabapentin compression formulations with different E PO levels compared with amino acids.
Figure 7:
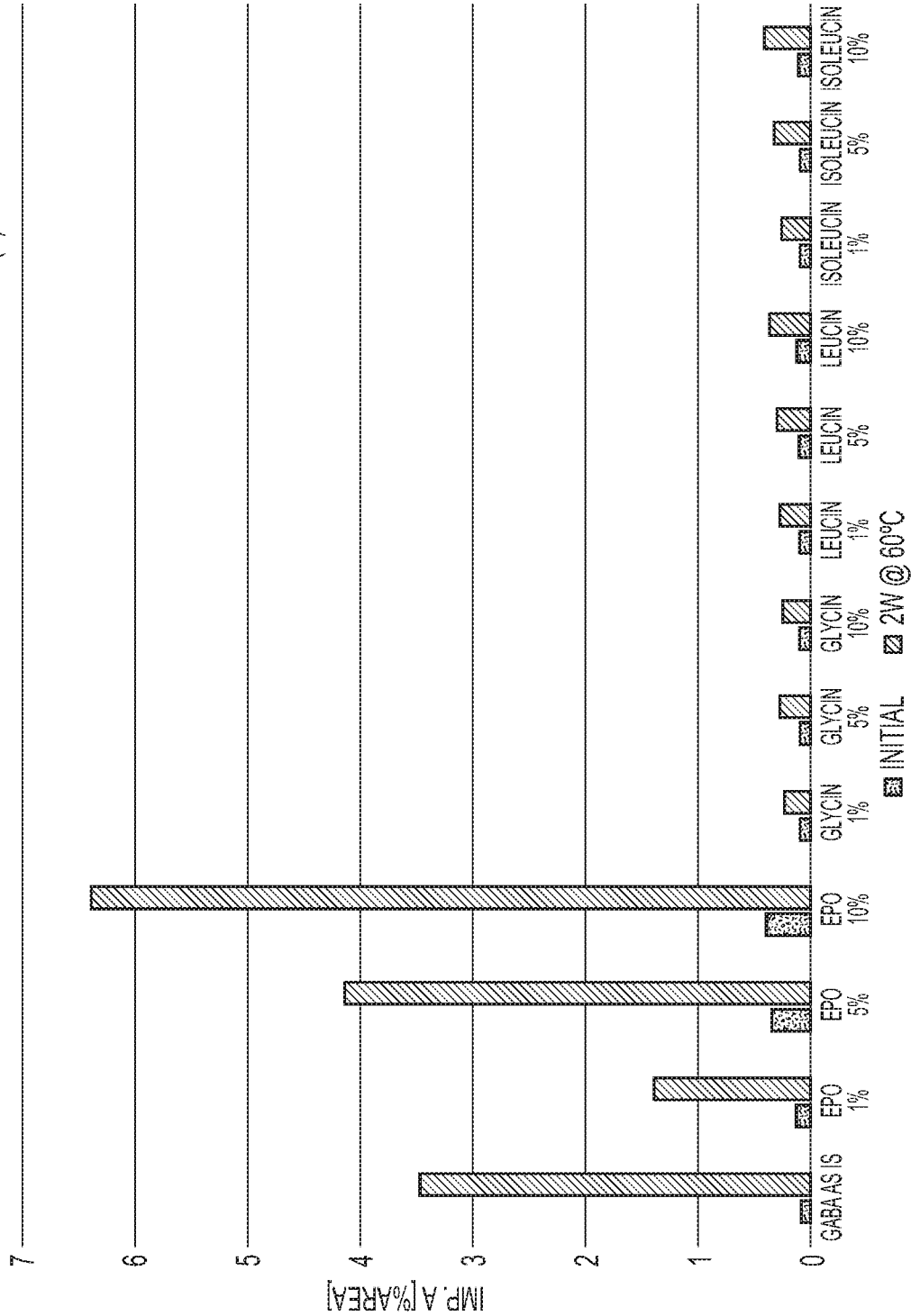
FIG. 7 is a graph of the formation of Impurity A at different storage times for various gabapentin ethanol granulation formulations with different E PO levels compared with amino acids.
Figure 8:
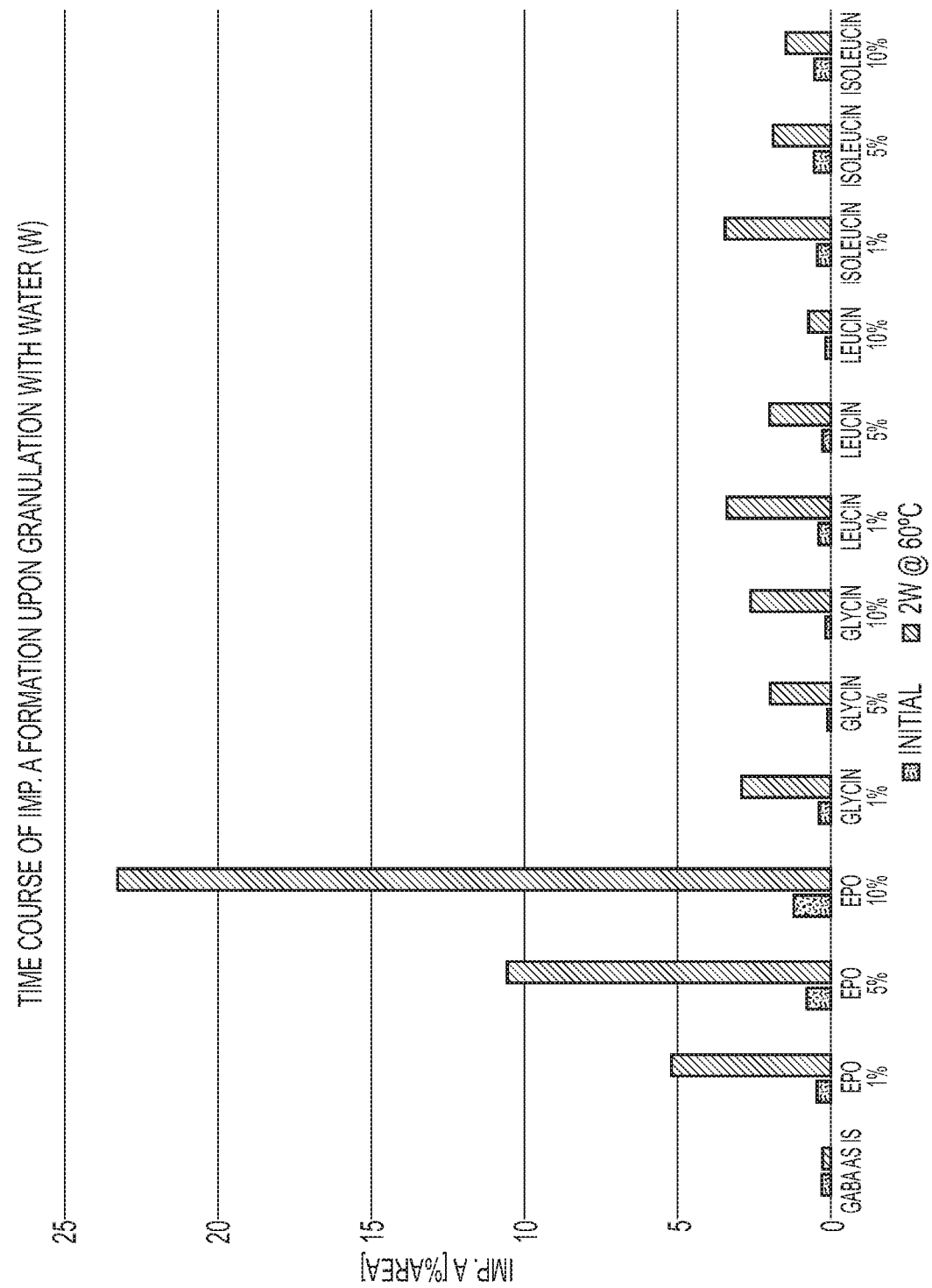
FIG. 8 is a graph of the formation of Impurity A at different storage times for various gabapentin water granulation formulations with different E PO levels compared with amino acids.
Figure 9:
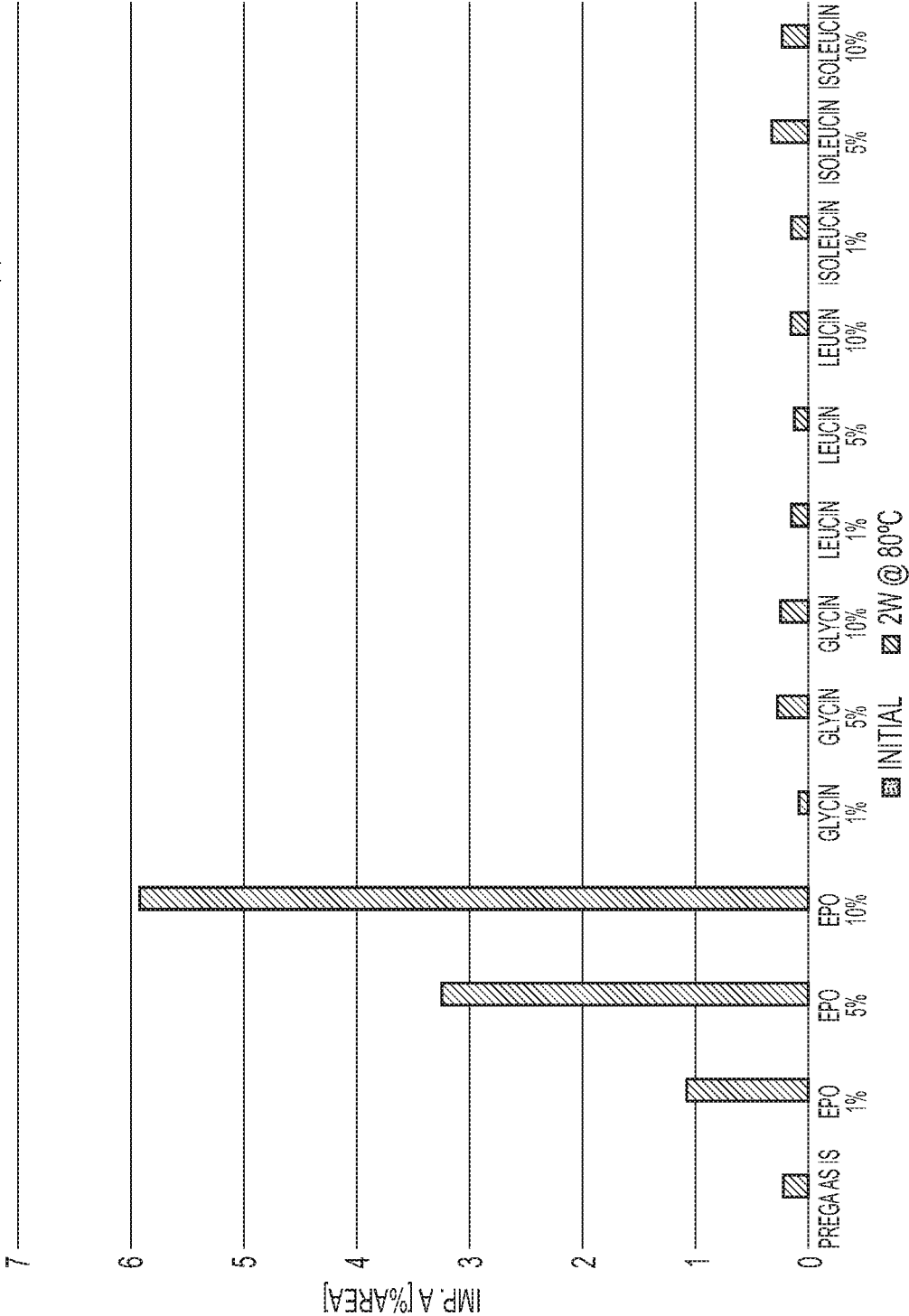
FIG. 9 is a graph of the formation of Impurity A at different storage times for various pregabalin mortar treatment formulations with different EPO levels compared with amino acids.
Figure 10:
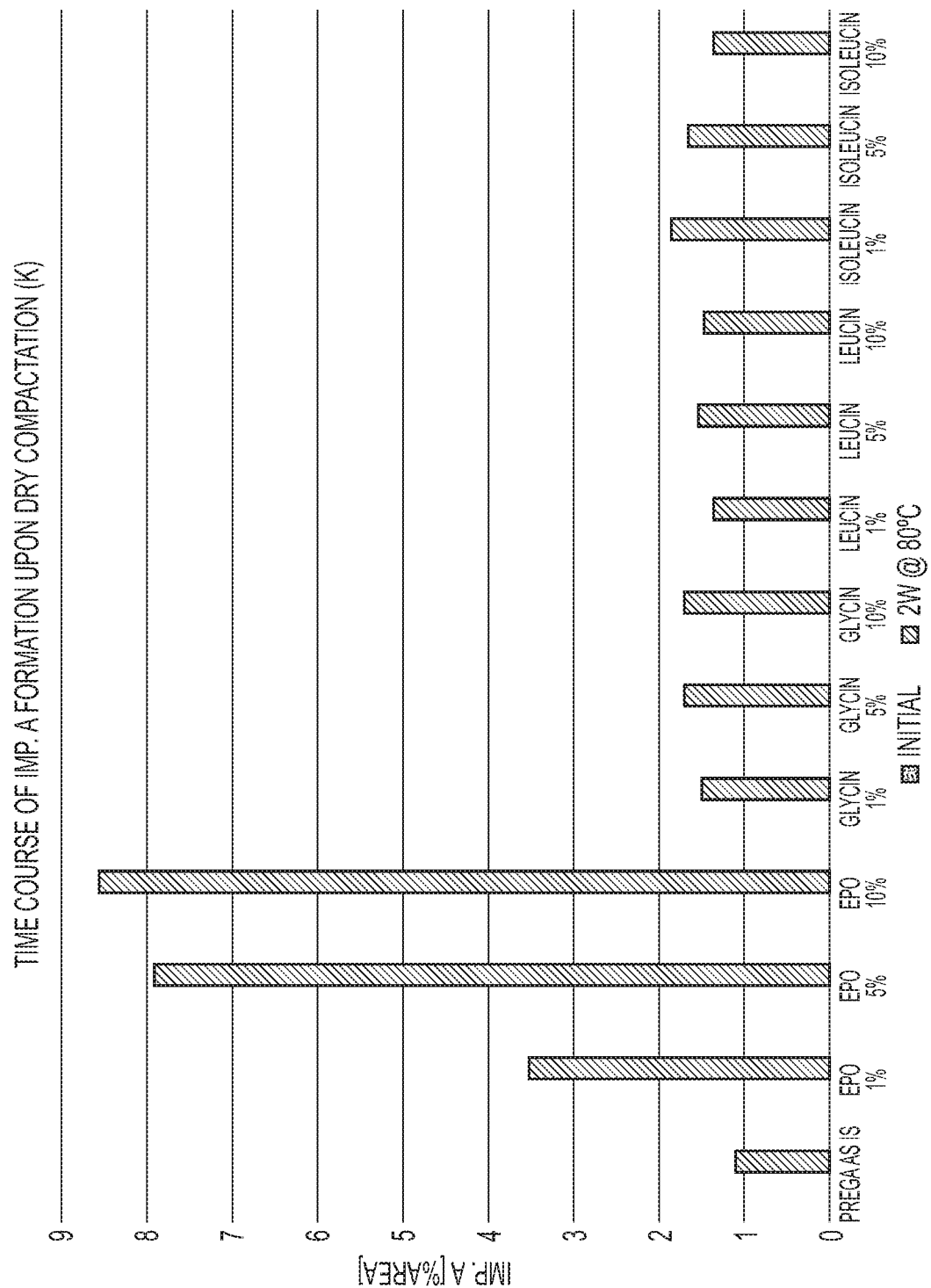
FIG. 10 is a graph of the formation of Impurity A at different storage times for various pregabalin compression formulations with different E PO levels compared with amino acids.
Figure 11:
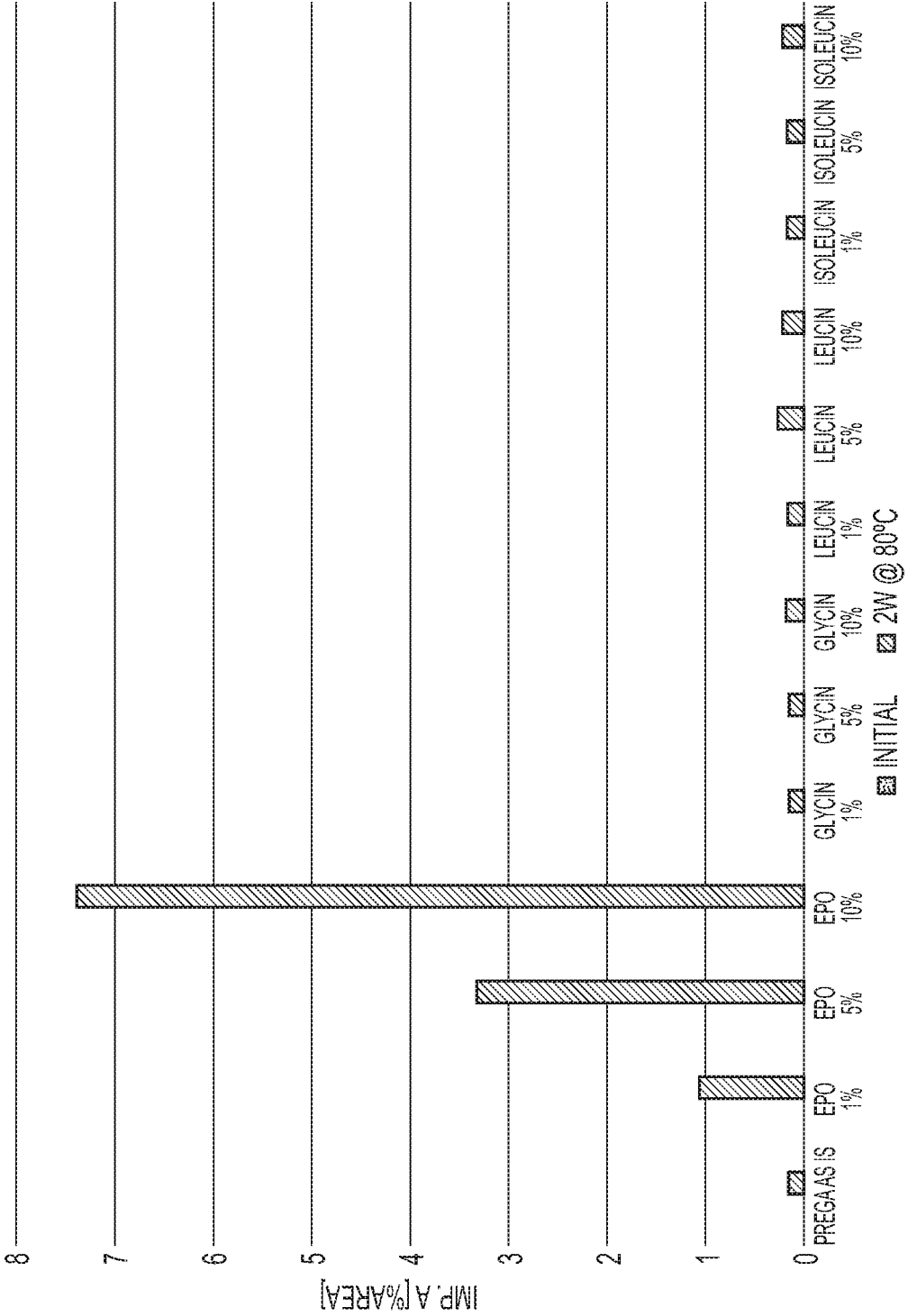
FIG. 11 is a graph of the formation of Impurity A at different storage times for various pregabalin ethanol granulation formulations with different E PO levels compared with amino acids.
Figure 12:
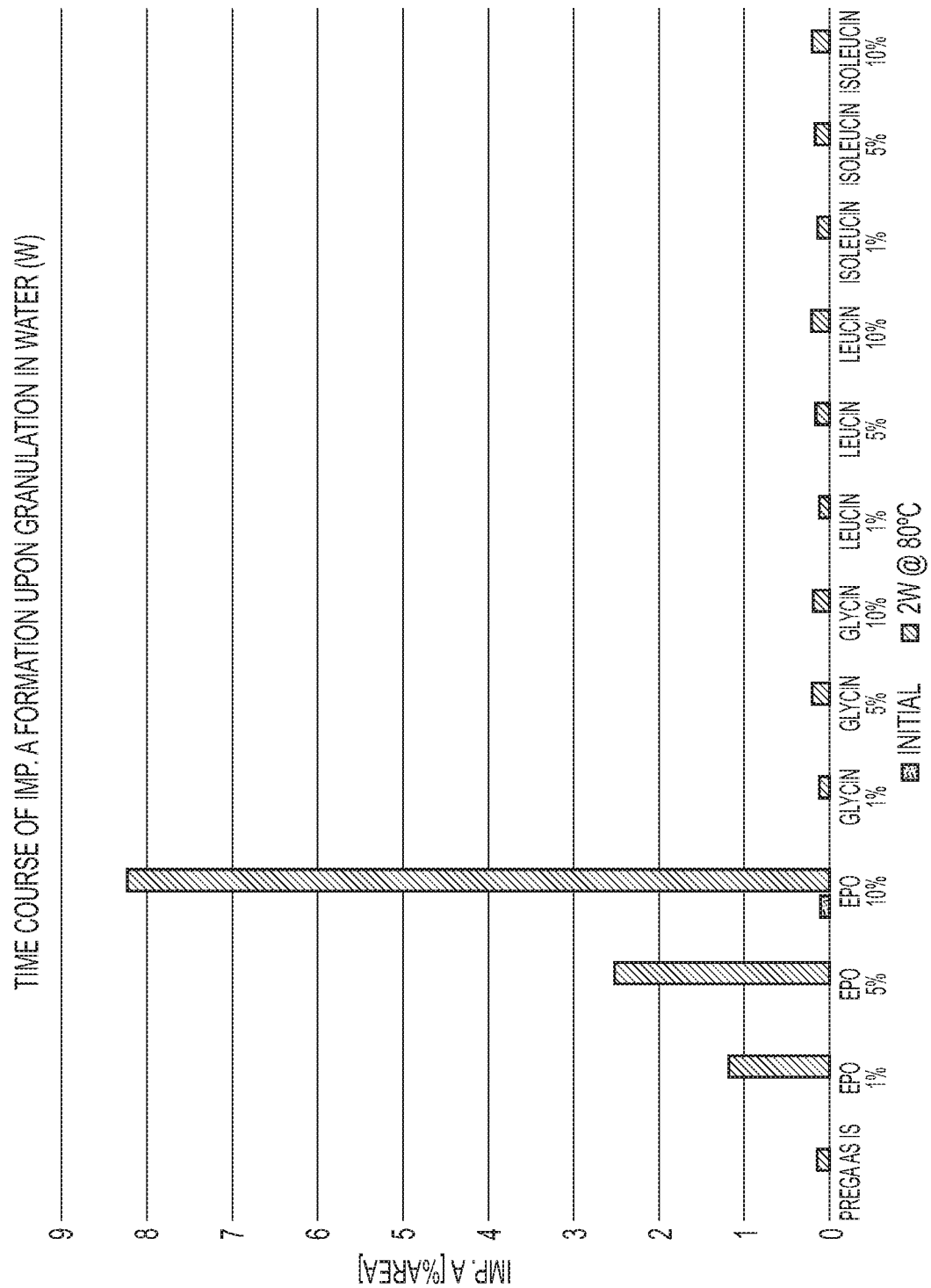
FIG. 12 is a graph of the formation of Impurity A at different storage times for various pregabalin water granulation formulations with different E PO levels compared with amino acids.

The particulars shown herein are by way of example and for purposes of illustrative discussion of the various embodiments of the present disclosure only, and provide what is believed to be the most useful and readily understood description of the principles and conceptual aspects of the disclosed subject matter. In this regard, no attempt is made to show details of the disclosed subject matter in more detail than is necessary for a fundamental understanding of the disclosure, the description making apparent to those skilled in the art how the several forms of the disclosure may be embodied in practice.

The following disclosure refers to more detailed embodiments, with occasional reference to the accompanying figures. The disclosed subject matter, however, may be embodied in different forms and should not be construed as limited to the embodiments set forth herein.

Unless otherwise defined, all technical and scientific terms used herein have the same meaning as commonly understood by one of ordinary skill in the art to which this disclosure belongs. The terminology used in the description herein is for describing particular embodiments only and is not intended to be limiting. As used in the specification and claims, the singular forms "a," "an," and "the" are intended to include the plural forms as well, unless the context clearly indicates otherwise. Also, the phrases "at least one" and "one or more" are intended to be interchangeable, and their use are not intended to limit the scope of any described or claimed feature preceded by "a," "an," and "the" to a singular form.

All publications, patent applications, patents, and other references mentioned herein are expressly incorporated by reference in their entirety, unless otherwise indicated.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and claims are approximations that may vary depending upon the desired properties sought to be obtained by a particular embodiment. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosed subject matter are approximations, the numerical values set forth in the specific examples are reported as precisely as possible. Any numerical value, however, inherently contains certain errors necessarily resulting from the standard deviation found in the method used to obtain the value. Every numerical range given throughout this specification includes every narrower numerical range that falls within such broader numerical range, as if such narrower numerical ranges were all expressly written herein.

Reference to compounds in the specification includes esters and salts of such compounds. Thus, even if not explicitly disclosed, such esters and salts are contemplated and encompassed by reference to the compounds themselves.

All percent measurements in this application, unless otherwise stated, are measured by weight based upon 100% of a given sample weight. Thus, for example, 30% represents 30 weight parts out of every 100 weight parts of the sample.

The present disclosure relates, in part, to a composition comprising an active ingredient, and a stabilizer. The composition may be a pharmaceutical composition.

A "pharmaceutical composition" as used herein means a composition comprising an active ingredient and at least one pharmaceutically acceptable excipient. As used herein, the term "pharmaceutically acceptable excipient" means a compound or ingredient that is compatible with the other ingredients in a pharmaceutical formulation and not injurious to an intended subject when administered in normal or therapeutically effective amounts. As used herein, an "intended subject" includes animals and/or humans. The terms "patient" and "subject" may be used interchangeably.

Suitable excipients are known to those of skill in the art and examples are described, for example, in the Handbook of Pharmaceutical Excipients (Kibbe (ed.), 3rd Edition (2000), American Pharmaceutical Association, Washington, D.C.), and Remington's Pharmaceutical Sciences (Gennaro (ed.), 20th edition (2000), Mack Publishing, Inc., Easton, Pa.), which, for their disclosures relating to excipients and dosage forms, are incorporated herein by reference. Examples of excipients include but are not limited to fillers, extenders, diluents, wetting agents, solvents, emulsifiers, preservatives, absorption enhancers, sustained-release matrices, starches, sugars, microcrystalline cellulose, granulating agents, lubricants, binders, disintegrating agents, coloring agents, release agents, coating agents, sweetening agents, flavoring agents, perfuming agents, antioxidants, plasticizers, gelling agents, thickeners, hardeners, setting agents, suspending agents, surfactants, humectants, carriers, stabilizers, and combinations thereof.

The present disclosure includes a large number and variety of components that are contemplated for inclusion in the pharmaceutical formulations. It should be recognized that when the inventors expressly contemplate including such components, they also expressly contemplate excluding such components. Thus, all components disclosed herein are expressly contemplated for exclusion as well.

As used herein, "active ingredient" is any component of the composition intended to furnish pharmacological activity or other direct effect in the diagnosis, cure, mitigation, treatment, or prevention of disease, or to affect the structure or any function of the body of the intended subject. Active ingredients include those components of the composition that may undergo chemical change during the manufacture of the composition and be present in a finished composition in a modified form intended to furnish the specified activity or effect. Active ingredients also include those components of the finished composition that during or after administration of the finished drug product to the intended user may undergo chemical change to a modified form intended to furnish the specified activity or effect. For example, the active ingredient can be a pharmaceutically acceptable salt of the component that furnishes the specified activity or effect.

As used herein, the term "pharmaceutically acceptable salt" includes salts that are physiologically tolerated by the intended subject. Such salts are typically prepared from an inorganic and/or organic acid. Examples of suitable inorganic acids include hydrochloric, hydrobromic, hydroiodic, nitric, sulfuric, and phosphoric acid. Organic acids may be aliphatic, aromatic, carboxylic, and/or sulfonic acids. Suitable organic acids include formic, acetic, propionic, succinic, camphorsulfonic, citric, fumaric, gluconic, lactic, malic, mucic, tartaric, para-toluenesulfonic, glycolic, glucuronic, maleic, furoic, glutamic, benzoic, anthranilic, salicylic, phenylacetic, mandelic, pamoic, methanesulfonic, ethanesulfonic, pantothenic, benzenesulfonic (besylate), stearic, sulfanilic, alginic, galacturonic, and the like.

The composition may contain only one active ingredient, or more than one active ingredient, such as two, three, four, five, six, seven, eight, or nine active ingredients, or more than nine active ingredients.

The active ingredient can be selected from among active pharmaceutical ingredients (APIs). An API is a substance or mixture of substances intended to be used in the manufacture of a pharmaceutical product and that, when used in the production of a pharmaceutical product, becomes an active ingredient of the pharmaceutical product. Such substances are intended to furnish pharmacological activity or other direct effect in the diagnosis, cure, mitigation, treatment, or prevention of disease or to affect the structure or function of the body of the intended subject.

In some embodiments, the active ingredient is a lactam-forming ingredient, such as a 4-amino-3-substituted-butanoic acid derivative. Examples of 4-amino-3-substituted-butanoic acid derivatives include baclofen, gabapentin, and pregabalin.

In some embodiments, the active ingredient is selected from baclofen (4-amino-3-(4-chlorophenyl)butanoic acid) and its pharmaceutically acceptable salts. Baclofen has the following structure:

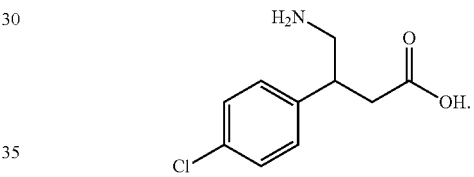

The active ingredient, such as baclofen, can be in any form, such as granular, powder, or micronized form (e.g., Micronized, USP from Polpharma). Without being bound to a particular scientific theory, the inventors hypothesize that smaller particle size results in larger surface area and increases the contact area between the baclofen and the stabilizer, improving the ability of the stabilizer to interact with and stabilize the baclofen. The active ingredient may be milled to reduce the particle size.

The average particle size of the active ingredient will generally be less than 1000 μm, such as less than 750 μm, less than 500 μm, less than 250 μm, or less than 125 μm. The average particle size may be larger than 25 μm, or larger than 50 μm, or larger than 75 μm, or larger than 100 μm, or larger than 125 μm, or larger than 150 μm. The average particle size will generally range from about 50 to about 750 μm, or from about 75 to about 500 μm, or from about 100 to about 200 μm. The average particle size is not critical, as long as the stabilizing effect is produced.

In addition to the active ingredient, the composition comprises a stabilizer that inhibits the formation of the lactam autodegradation product of a 4-amino-3-substituted-butanoic acid derivative, or its pharmaceutically acceptable salt, when used as an active ingredient. The main lactam autodegradation product of baclofen is 4-(4-chlorophenyl)-2-pyrrolidine (4-CPP) (also referred to herein as "Impurity A").

As used herein, the term "stabilizer" refers to the compound or compounds in the composition that functions to reduce or inhibit the formation of the lactam autodegradation product of a 4-amino-3-substituted-butanoic acid derivative or its pharmaceutically acceptable salt. In embodiments, the term "stabilizer" excludes the α-amino acids described by U.S. Pat. No. 7,309,719 as stabilizers, including any of the following:

neutral α-amino acids including glycine, phenylglycine, hydroxyphenylglycine, dihydroxyphenylglycine, L-alanine, hydroxy-L-alanine, L-leucine, hydroxy-L-leucine, dihydroxy-L-leucine, L-norleucine, methylene-L-norleucine, L-ketonorleucine, L-isoleucine, hydroxy-L-isoleucine, dihydroxy-L-isoleucine, L-valine, hydroxy-L-valine, L-isovaline, L-norvaline, hydroxy-L-norvaline, hydroxy-L-ketonorvaline, L-methionine, L-homomethionine, L-ethionine, L-threonine, acetyl-L-threonine, L-tryptophan, hydroxy-L-tryptophan, methyl-L-tryptophan, L-tyrosine, hydroxy-L-tyrosine, methyl-L-tyrosine, bromo-L-tyrosine, dibromo-L-tyrosine, 3,5-diiodo-L-tyrosine, acetyl-L-tyrosine, chloro-L-tyrosine, L-m-tyrosine, L-levodopa, L-methyldopa, L-thyroxine, L-serine, acetyl-L-serine, L-homoserine, acetyl-L-homoserine, ethyl-L-homoserine, propyl-L-homoserine, butyl-L-homoserine, L-cystine, L-homocystine, methyl-L-cystein, allyl-L-cysteine, propyl-L-cysteine, L-phenylalanine, dihydro-L-phenylalanine, hydroxymethyl-L-phenylalanine, L-aminobutyric acid, L-aminoisobutyric acid, L-ketoaminobutyric acid, dichloro-L-aminobutyric acid, dihydroxy-L-aminobutyric acid, phenyl-L-aminobutyric acid, L-aminovaleric acid, L-aminohydroxyvaleric acid, dihydroxy-L-aminovaleric acid, L-aminoisovaleric acid, L-aminohexanoic acid, methyl-L-aminohexanoic acid, L-aminoheptanoic acid, L-aminooctanoic acid, citrulline, and the D- and DL-forms thereof;

acidic α-amino acids including L-aspartic acid, L-glutamic acid, L-carbocysteine, L-aminoglutaric acid, L-aminosuccinic acid, L-aminoadipic acid, L-aminopimelic acid, hydroxy-L-aminopimelic acid, methyl-L-aspartic acid, hydroxy-L-aspartic acid, methyl-L-glutamic acid, methyl-hydroxy-L-glutamic acid, L-methyleneglutamic acid, hydroxy-L-glutamic acid, dihydroxy-L-glutamic acid, hydroxy-L-aminoadipic acid, and the like, and the D- and DL-forms thereof;

basic α-amino acids including L-arginine, L-lysine, L-ornithine, L-canavanine, L-canaline, hydroxy-L-lysine, L-homoarginine, hydroxy-L-homoarginine, hydroxy-L-ornithine, L-diaminopropionic acid, L-diaminohexanoic acid, L-diaminobutyric acid. L-diaminovaleric acid, L-diaminoheptanoic acid, L-diaminooctanoic acid, and the like and the D- and DL-forms thereof; and α,Ω-diaminodicarboxylic acids including diaminosuccinic acid, diaminoglutaric acid, diaminoadipic acid, diaminopimelic acid, and the like.

The stabilizer may be selected from polymethacrylate-based copolymers, which may include anionic, cationic, and neutral copolymers based on methacrylic acid and methacrylic/acrylic esters or their derivatives, including, but not limited to, amino methacrylate copolymers, methyl methacrylate copolymers, dimethylaminoethyl methacrylate copolymers, and butyl methacrylate copolymers, in particular, methacrylic ester copolymer, methacrylic acid copolymer, ammonioalkyl methacrylate copolymer, and amino alkyl methacrylate copolymer. In some embodiments, the stabilizer is poly(butylmethacrylate-co-(2-dimethylaminoethyl)methacrylate-co-methyl methacrylate.

The manner of mixing the active ingredient and stabilizer is not critical, and can be done in any pharmaceutically acceptable manner. Tumbler, convective, and fluidization blenders are useful, for example, where the active ingredient and stabilizer are mixed in dry form; agitators and heavy mixers, including high shear mixers, are useful, for example, where the active ingredient and stabilizer are mixed with a liquid. The composition can be made into a granular formulation, through wet or dry granulation, depending on the desired dosage form, release rate, or other manufacturing preferences.

Wet granulation solvents can be selected based on the preference of the manufacturer and are not critical. Examples include, but are not limited to, ethanol and water. If desired, binders such as PVP can also be included.

In some embodiments, the formulation is manufactured in such a way as to maximize the interaction between molecules of the active ingredient and molecules of the stabilizer. This may take the form of a matrix formulation in which the active ingredient and stabilizer are intimately mixed, and may be based on starting materials in which the active ingredient is milled to increase its surface area and interaction with the stabilizer. Without wishing to be bound by any particular theory of operation, it appears that the stabilizing effect is through a chemical interaction between the stabilizing agent and the active ingredient. Thus, steps that increase the ability of the stabilizing agent and active ingredient are believed to be helpful in maximizing the stabilizing effect.

In a wet granulation process, the active agent and stabilizer can be intimately mixed by dry blending, followed by adding a granulation solvent. This process is intended to improve the interaction between the active ingredient and the stabilizer, and is distinguished from processes in which a polymer is first dissolved in a solvent, followed by mixing with a dry active ingredient.

Those skilled in the art will readily recognize that a matrix having the above-described intimate mixture of active ingredient and stabilizer is structurally different from coated or encapsulated active ingredients, as such are commonly understood in the art. That is, a coated or encapsulated product is one in which a core containing the active ingredient is completely encased in or covered by the coating material. Such a structure does not maximize the interaction between the active ingredient and stabilizer.

On the other hand, an intimate mixture of stabilizer and active ingredient in matrix granules can have some active ingredient at the outer periphery of the granule that is not completely covered by the stabilizer. Such a matrix in accordance with the present disclosure is not designed to coat or encase the active ingredient, but is rather intended to maximize interaction between active ingredient and stabilizer. However, to be clear, the inventors contemplate that granules formed from an intimate mixture of stabilizer and active ingredient (i.e., a stabilized composition of the active ingredient) can be further coated with a coating material (examples of which are discussed in more detail below) for a variety of effects.

The composition comprising the intimate mixture of active ingredient and stabilizer may contain a weight ratio of the stabilizer to the active ingredient in a range from about 1:100 to about 20:1, such as from about 1:10 to about 10:1, about 9:1 to about 20:1, about 0.01:1 to about 7:1, about 6:1 to about 13:1, about 12:1 to about 20:1, about 0.5:1 to about 10:1, about 1:1 to about 7:1, about 1.5:1 to about 18:1, about 1.6:1 to about 20:1, or about 1.8:1 to about 7.5:1, with specific examples being 1.6:1, 1.7:1, 1.8:1, 1.9:1, 2:1, 2.1:1, 2.4:1, 2.6:1, 3:1, 4:1, and 5:1. The lower limit of the range may be any value from about 0.01:1 or greater, and the upper limit of the range may independently be any value from about 20:1 or less, so long as the lower limit is not greater than the upper limit.

The composition may be formulated by varying the ratios of the active ingredient and stabilizer, both in powder form. Alternatively, "active granules" may be formulated to include both active ingredient and stabilizer, and "placebo granules" may be formulated without active ingredient, and the final ratios may be varied by adjusting ratios of the two types of granules. In some embodiments, the placebo granules contain approximately the same amount of stabilizer and excipients present in the active granules (i.e. granules of the intimate mixture of active ingredient and stabilizer). The missing active ingredient may be substituted with an additional amount of one of the excipients in an amount equal to that of the missing active ingredient to maintain the ratios of the other ingredients in the placebo granules. The placebo granules may have the same average diameter as the active granules. Different strengths of dosage forms can be obtained my mixing non-placebo granules with placebo granules.

Pharmaceutical compositions are typically provided in dosage forms that are suitable for administration to an intended subject by a desired route. Various dosage forms are described below, but are not meant to include all possible choices. One of skill in the art is familiar with the various dosage forms that are suitable for use, as described, for example, in Remington's Pharmaceutical Sciences, which has been incorporated by reference above. The most suitable route in any given case will depend on the nature and severity of the disease and/or condition being prevented, treated, and/or managed. For example, pharmaceutical compositions may be formulated for administration orally, nasally, rectally, intravaginally, parenterally, intracisternally, and topically, including buccally and sublingually.

Formulations for oral administration include capsules, cachets, pills, tablets, lozenges (using a flavored basis, usually sucrose and acacia or tragacanth), powders, granules, suspensions in an aqueous or non-aqueous liquid, oil-in-water or water-in-oil liquid emulsions, elixirs, syrups, pastilles (using an inert base, such as gelatin and glycerin, or sucrose and acacia), mouth washes, pastes, and the like; each containing a predetermined amount of stabilizer and baclofen, a derivative thereof, or a pharmaceutically acceptable salt thereof, to provide a therapeutic amount of the baclofen in one or more doses.

Liquid dosage forms may include the stabilized formulations according to the present invention in suspension form. For example, coated or uncoated stabilized granules may be suspended in a liquid for administration. A suspension may be manufactured as a suspension or reconstituted by an end user (e.g., doctor, pharmacist, patient) as a suspension for administration. The inventors also contemplate the reconstitution of a stabilized formulation by dissolving a stabilized formulation in a liquid that dissolves the stabilized formulation. This too could be mixed by the manufacturer, or by an end user.

In solid dosage forms for oral administration (capsules, tablets, pills, powders, granules and the like), the active ingredient, derivative thereof, or pharmaceutically acceptable salt thereof can be mixed with one or more pharmaceutically-acceptable excipients, including carriers, such as sodium citrate or dicalcium phosphate; fillers or extenders, such as starches, spray-dried or anhydrous lactose, sucrose, glucose, mannitol, dextrose, sorbitol, xylitol, cellulose, dehydrated or anhydrous dibasic calcium phosphate, and/or silicic acid; binders, such as acacia, alginic acid, carboxymethylcellulose (sodium), cellulose (microcrystalline), dextrin, ethylcellulose, gelatin, glucose (liquid), guar gum, hydroxypropyl cellulose, hydroxypropyl methylcellulose, methylcellulose, polyethylene oxide, povidone, starch (pregelatinized) or syrup; humectants, such as glycerol; disintegrating agents, such as agar, calcium carbonate, potato or tapioca starch, alginic acid, certain silicates, pregelatinized starch, sodium starch glycolate, crosslinked povidone, crosslinked sodium carboxymethylcellulose, clays, microcrystalline cellulose, alginates, gums, and/or sodium carbonate; solution retarding agents, such as paraffin; absorption accelerators, such as quaternary ammonium compounds; wetting agents, such as cetyl alcohol or glycerol monostearate; absorbents, such as kaolin and bentonite clay; lubricants, such as talc, calcium stearate, magnesium stearate, solid polyethylene glycols, steric acid, sodium stearyl fumarate, magnesium lauryl sulfate, hydrogenated vegetable oil, and/or sodium lauryl sulfate; glidants, such as calcium silicate, magnesium silicate, colloidal anhydrous silica, and/or talc; flavoring agents, such as synthetic flavor oils and flavoring aromatics, natural oils, extracts from plant leaves, flowers, and fruits, including cinnamon oil, oil of wintergreen, peppermint oils, bay oil, anise oil, eucalyptus, thyme oil, vanilla, citrus oil (e.g., lemon, orange, grape, lime, and grapefruit), fruit essences (e.g., apple, banana, pear, peach, strawberry, raspberry, cherry, plum, pineapple, apricot, as so forth); coloring agents and/or pigments, such as titanium dioxide and/or dyes approved for use in food and pharmaceuticals; buffering agents; dispersing agents; preservatives; and/or diluents.

Solid dosage forms may optionally be scored or prepared with coatings and shells, such as enteric coatings, and coatings for modifying the rate of release, examples of which are well known in the pharmaceutical-formulating art. For example, such coatings may comprise sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, wax, or zein. The coating material may further comprise anti-adhesives, such as talc; plasticizers, such as castor oil, diacetylated monoglycerides, dibutyl sebacate, diethyl phthalate, glycerin, polyethylene glycol, propylene glycol, triacetin, triethyl citrate; opacifiers, such as titanium dioxide; and/or coloring agents and/or pigments. The coating process may be carried out by any suitable means, for example, by using a perforated pan system.

Tablets may be formed by any suitable process, examples of which are known to those of ordinary skill in the art. For example, the ingredients may be dry-granulated or wet-granulated, such as with water or ethanol, by mixing in a suitable apparatus before tableting. Granules of the ingredients to be tableted may also be prepared using suitable spray/fluidization or extrusion/spheronization techniques.

With quick-release tablets, the choice of excipients generally allows a fast dissolution. The tablets may be conventional instant release tablets designed to be taken whole in the typical administration manner (i.e., with a sufficient amount of water to facilitate swallowing). Alternatively, the tablets may be formulated with suitable excipients to act as a fast dissolving and/or fast melting tablet in the oral cavity. Xylitol is especially useful as an excipient in orally disintegrating formulations. Also, the tablet can be in the form of a chewable or effervescent dosage form. With effervescent dosage forms, the tablet is typically added to a suitable liquid that causes it to disintegrate, dissolve, and/or disperse.

Tablets typically are designed to have an appropriate hardness and friability to facilitate manufacture on an industrial scale using equipment to produce tablets at high speed. Also, the tablets can be packed or filled in all kinds of containers. If the tablet has an insufficient hardness or is friable, the tablet that is taken by the subject or patient may be broken or crumbled into powder. Because of this insufficient hardness or friability, the subject or patient can no longer be certain that the amount of the dose is correct. The hardness of tablets, disintegration rate, and other properties can be influenced by the shape of the tablets. Tablets may be circular, oblate, oblong, or any other pharmaceutically acceptable shape.

Solid compositions may be encapsulated in a soft or hard gelatin capsule using any of the excipients described here. For example, an encapsulated dosage form may include fillers, such as lactose and microcrystalline; glidants, such as colloidal silicon dioxide and talc; lubricants, such as magnesium stearate; and disintegrating agents, such as starch (e.g., maize starch). Using capsule filling equipment, the ingredients to be encapsulated can be milled together, sieved, mixed, packed together, and then delivered into a capsule.

The compositions include immediate release, modified release, sustained release, and controlled release formulations and dosage forms, and any combination thereof.

As used herein, the term "immediate release" describes a formulation or dosage form that releases the drug upon dissolution, without significant delay. In some embodiments, such formulations would release the drug in the upper GI, including the mouth, esophagus, and/or stomach.

Different types of modified dosage forms are briefly described below. A more detailed discussion of such forms may also be found in, for example, The Handbook of Pharmaceutical Controlled Release Technology, D. L. Wise (ed.), Marcel Dekker, Inc., New York (2000); and also in Treatise on Controlled Drug Delivery: Fundamentals, Optimization, and Applications, A. Kydonieus (ed.), Marcel Dekker, Inc., New York, (1992), the relevant contents of each of which is hereby incorporated by reference for this purpose. Examples of modified release dosage forms are also described, for example, in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, the disclosures of which, for their discussions of pharmaceutical formulations, are incorporated herein by reference.

As used herein, the phrase "modified-release" describes a formulation or dosage form that achieves a desired release of the drug from the formulation. For example, a modified-release formulation may extend the influence or effect of a therapeutically effective dose of a pharmaceutically active compound in a patient. Such formulations are referred to herein as "extended-release formulations." In addition to maintaining therapeutic levels of the pharmaceutically active compound, a modified-release formulation may also be designed to delay the release of the active compound for a specified period. Such compounds are referred to herein as "delayed onset" of "delayed release" formulations or dosage forms. Still further, modified-release formulations may exhibit properties of both delayed and extended release formulations, and thus be referred to as "delayed-onset, extended-release" formulations.

Advantages of modified-release formulations may include extended activity of the drug, reduced dosage frequency, increased patient compliance, and the ability to deliver the drug to specific sites in the intestinal tract. Suitable components (e.g., polymers, excipients, etc.) for use in modified-release formulations, and methods of producing the same, are also described, e.g., in U.S. Pat. No. 4,863,742, which is incorporated by reference for these purposes.

Modified release formulations can be provided as matrix-based dosage forms. Matrix formulations may include hydrophilic, e.g., water-soluble, and/or hydrophobic, e.g., water-insoluble, polymers. Matrix formulations may optionally be prepared with functional coatings, which may be enteric, e.g., exhibiting a pH-dependent solubility, or non-enteric, e.g., exhibiting a pH-independent solubility.

Matrix formulations may be prepared by using, for example, direct compression or wet granulation. A functional coating, as noted above, may then be applied. Additionally, a barrier or sealant coat may be applied over a matrix tablet core prior to application of a functional coating. The barrier or sealant coat may serve the purpose of separating an active ingredient from a functional coating, which may interact with the active ingredient, or it may prevent moisture from contacting the active ingredient. Details of barriers and sealants are provided below. There is no limit on the manners in which the various features described herein may be combined, provided that the formulation is a stabilized formulation.

The inventors contemplate that a matrix composition of the stabilized formulation may be formed by mixing the active ingredient with a stabilizer, and forming that composition into a solid dosage form, such as a multi-unit-containing capsule or a monolithic tablet. The inventors also contemplate the use of other excipients, such as polymers, that may be used to modify the release of the active agent from the formulation.

In a matrix-based dosage form, for example, the active ingredient, stabilizer, and optional pharmaceutically acceptable excipients may be dispersed within one or more polymers. The one or more polymers typically comprise at least one water-soluble polymer and/or at least one water-insoluble polymer. The active ingredient may be released from the dosage form by diffusion and/or erosion.

Water-soluble polymers include polyvinyl alcohol, polyvinylpyrrolidone, methylcellulose, hydroxypropylcellulose, hydroxypropylmethylcellulose, or polyethylene glycol, and/or mixtures thereof.

Water-insoluble polymers include ethylcellulose, cellulose acetate cellulose propionate, cellulose acetate propionate, cellulose acetate butyrate, cellulose acetate phthalate, cellulose triacetate, poly(methyl) in more than one group; the classifications are descriptive only, and not intended to limit any use of a particular excipient.

The amounts and types of polymers, and the ratio of water-soluble polymers to water-insoluble polymers in formulations can be selected to achieve a desired release profile of the active ingredient, a derivative thereof or a pharmaceutically acceptable salt thereof. For example, by increasing the amount of water-insoluble-polymer relative to the amount of water-soluble polymer, the release of the drug may be delayed or slowed. This is due, in part, to an increased impermeability of the polymeric matrix, and, in some cases, to a decreased rate of erosion during transit through the GI tract.

Modified release formulations may also be provided as membrane-controlled formulations. Membrane controlled formulations can be made by preparing a rapid release core, which may be a monolithic (e.g., tablet) or multi-unit (e.g., pellet) type, and coating the core with a membrane. The membrane-controlled core can then be further coated with a functional coating. In between the membrane-controlled core and functional coating, a barrier or sealant may be applied. Details of membrane-controlled dosage forms are provided below.

Modified release formulations can comprise at least one polymeric material, which may be applied as a membrane coating to active ingredient-containing granule cores. Suitable water-soluble polymers include polyvinyl alcohol, polyvinylpyrrolidone, methylcellulose, hydroxypropylcellulose, hydroxypropylmethylcellulose, polyethylene glycol, and/or mixtures thereof.

Suitable water-insoluble polymers include ethylcellulose, cellulose acetate cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), and poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(ethylene oxide), poly(ethylene terephthalate), poly(vinyl isobutyl ether), poly(vinyl acetate), poly(vinyl chloride) or polyurethane, and/or mixtures thereof. Methacrylate copolymers, such as EUDRAGIT™ polymers (available from Rohm Pharma) are polymeric lacquer substances based on acrylates and/or methacrylates. A variety of methacrylate copolymers are readily available, examples of which are described above. Certain methacrylate copolymers may serve as stabilizing agents in the present invention, but methacrylate copolymers may also be used to modify the release of the active ingredient. In this regard, it should be noted that not all methacrylate copolymers are believed to impart a stabilizing effect, but all methacrylate copolymers are believed to be useful for modifying the release of the active ingredient from the formulation.

The membrane coating may comprise a polymeric material comprising a major proportion (i.e., greater than 50% of the total polymeric content) of one or more pharmaceutically acceptable water-soluble polymers, and optionally a minor proportion (i.e., less than 50% of the total polymeric content) of one or more pharmaceutically acceptable water-insoluble polymers. Alternatively, the membrane coating may comprise a polymeric material comprising a major proportion (i.e., greater than 50% of the total polymeric content) of one or more pharmaceutically acceptable water-insoluble polymers, and optionally a minor proportion (i.e., less than 50% of the total polymeric content) of one or more pharmaceutically acceptable water-soluble polymers.

The coating membrane may further comprise at least one soluble excipient to increase the permeability of the polymeric material. Suitably, the soluble excipient is selected from among a soluble polymer, a surfactant, an alkali metal salt, an organic acid, a sugar, and a sugar alcohol. Such soluble excipients include polyvinyl pyrrolidone, polyethylene glycol, sodium chloride, surfactants such as sodium lauryl sulfate and polysorbates, organic acids such as acetic acid, adipic acid, citric acid, fumaric acid, glutaric acid, malic acid, succinic acid, and tartaric acid, sugars such as dextrose, fructose, glucose, lactose and sucrose, sugar alcohols such as lactitol, maltitol, mannitol, sorbitol and xylitol, xanthan gum, dextrins, and maltodextrins. In some embodiments, polyvinyl pyrrolidone, mannitol, and/or polyethylene glycol can be used as soluble excipients. The soluble excipient(s) may be used in an amount of from about 1% to about 10% by weight, based on the total dry weight of the polymer.

In some embodiments, the polymeric material comprises at least one water-insoluble polymer, which is also insoluble in gastrointestinal fluids, and at least one water-soluble pore-forming compound. For example, the water-insoluble polymer may comprise a terpolymer of polyvinylchloride, polyvinylacetate, and/or polyvinylalcohol. Suitable water-soluble pore-forming compounds include saccharose, sodium chloride, potassium chloride, polyvinylpyrrolidone, and/or polyethyleneglycol. The pore-forming compounds may be uniformly or randomly distributed throughout the water-insoluble polymer. Typically, the pore-forming compounds comprise about 1 part to about 35 parts for each about 1 to about 10 parts of the water-insoluble polymers.

When such dosage forms come in to contact with the dissolution media (e.g., intestinal fluids), the pore-forming compounds within the polymeric material dissolve to produce a porous structure through which the drug diffuses. Such formulations are described in more detail in U.S. Pat. No. 4,557,925, which relevant part is incorporated herein by reference for this purpose. The porous membrane may also be coated with an enteric coating, as described herein, to inhibit release in the stomach.

The polymeric material may also include one or more auxiliary agents such as fillers, plasticizers, and/or anti-foaming agents. Representative fillers include talc, fumed silica, glyceryl monostearate, magnesium stearate, calcium stearate, kaolin, colloidal silica, gypsum, micronized silica, and magnesium trisilicate. The quantity of filler used typically ranges from about 2% to about 300% by weight, and can range from about 20 to about 100%, based on the total dry weight of the polymer. In one embodiment, talc is the filler.

Coating membranes, and functional coatings as well, can also include a material that improves the processing of the polymers. Such materials are generally referred to as plasticizers and include, for example, adipates, azelates, benzoates, citrates, isoebucates, phthalates, sebacates, stearates and glycols. Representative plasticizers include acetylated monoglycerides, butyl phthalyl butyl glycolate, dibutyl tartrate, diethyl phthalate, dimethyl phthalate, ethyl phthalyl ethyl glycolate, glycerin, ethylene glycol, propylene glycol, triacetin citrate, triacetin, tripropinoin, diacetin, dibutyl phthalate, acetyl monoglyceride, polyethylene glycols, castor oil, triethyl citrate, polyhydric alcohols, acetate esters, glycerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate, and glyceryl monocaprate. In one embodiment, the plasticizer is dibutyl sebacate. The amount of plasticizer used in the polymeric material typically ranges from about 10% to about 50%, for example, about 10%, 20%, 30%, 40%, or 50%, based on the weight of the dry polymer.

Anti-foaming agents can also be included. The amount of anti-foaming agent used typically is from about 0% to about 0.5% of the final formulation.

The amount of polymer used in membrane-controlled formulations is typically adjusted to achieve the desired drug delivery properties, including the amount of drug to be delivered, the rate and location of drug delivery, the time delay of drug release, and the size of the multiparticulates in the formulation. The amount of polymer applied typically provides an about 10% to about 100% weight gain to the cores, such as from about 25% to about 70%.

The combination of all solid components of the polymeric material, including co-polymers, fillers, plasticizers, and optional excipients and processing aids, typically provides an about 10% to about 450% weight gain on the cores, such as from about 30% to about 160%.

The polymeric material can be applied by any known method, for example, by spraying using a fluidized bed coater (e.g., Wurster coating) or pan coating, or spray drying system. Coated cores are typically dried or cured after application of the polymeric material. Curing means that the multiparticulates are held at a controlled temperature for a time sufficient to provide stable release rates. Curing can be performed, for example, in an oven or in a fluid bed drier. Curing can be carried out at any temperature above room temperature.

A sealant or barrier can also be applied to the polymeric coating. A sealant or barrier layer may also be applied to the core prior to applying the polymeric material. A sealant or barrier layer is not intended to modify the release of baclofen, a derivative thereof or a pharmaceutically acceptable salt. Suitable sealants or barriers are permeable or soluble agents such as hydroxypropyl methylcellulose, hydroxypropyl cellulose, hydroxypropyl ethylcellulose, and xanthan gum.

Other agents can be added to improve the processability of the sealant or barrier layer. Such agents include talc, colloidal silica, polyvinyl alcohol, titanium dioxide, micronized silica, fumed silica, glycerol monostearate, magnesium trisilicate and magnesium stearate, or a mixture thereof. The sealant or barrier layer can be applied from solution (e.g., aqueous) or suspension using any known means, such as a fluidized bed coater (e.g., Wurster coating) or pan coating system. Suitable sealants or barriers include, for example, OPADRY WHITE Y-1-7000® (a mixture of titanium dioxide, hydroxypropyl cellulose, and polyethylene glycol) and OPADRY OY/B/28920 WHITE® (polyvinyl alcohol, titanium dioxide, talc, lecithin, and xanthan gum), each of which is available from Colorcon Limited, England.

The composition may be an oral dosage form containing a multi-particulate active ingredient in the form of caplets, capsules, particles for suspension prior to dosing, sachets, or tablets. When the dosage form is in the form of tablets, the tablets may be disintegrating tablets, fast dissolving tablets, effervescent tablets, fast melt tablets, and/or mini-tablets. The dosage form can be of any shape suitable for oral administration of a drug, such as spheroidal, cube-shaped oval, or ellipsoidal. Dosage forms can be prepared from the multi-particulates in a manner known in the art and include additional pharmaceutically acceptable excipients, as desired.

Dosage forms may be monolithic and/or multi-unit dosage forms. Dosage forms may have a functional coating. Such coatings generally serve the purpose of delaying the release of the drug for a predetermined period. For example, such coatings may allow the dosage form to pass through the stomach without being subjected to stomach acid or digestive juices. Thus, such coatings may dissolve or erode upon reaching a desired point in the gastrointestinal tract, such as the upper intestine.

Such functional coatings may exhibit pH-dependent or pH-independent solubility profiles. Those with pH-independent profiles generally erode or dissolve away after a predetermined period, and the period is generally directly proportional to the thickness of the coating. Those with pH-dependent profiles, on the other hand, may maintain their integrity while in the acid pH of the stomach, but quickly erode or dissolve upon entering the more basic upper intestine.

Thus, a matrix-based, osmotic pump-based, or membrane-controlled formulation may be further coated with a functional coating that delays the release of the drug. For example, a membrane-controlled formulation may be coated with an enteric coating that delays the exposure of the membrane-controlled formulation until the upper intestine is reached. Upon leaving the acidic stomach and entering the more basic intestine, the enteric coating dissolves. The membrane-controlled formulation then is exposed to gastrointestinal fluid, and then releases baclofen, a derivative thereof or a pharmaceutically acceptable salt thereof over an extended period, in accordance with the invention. Examples of functional coatings such as these are well known to those in the art.

Any of the oral dosage forms described herein may be provided in the form of caplets, capsules, beads, granules, particles for suspension prior to dosing, sachets, or tablets. When the dosage form is in the form of tablets, the tablets may be disintegrating tablets, fast dissolving tablets, effervescent tablets, fast melt tablets, and/or mini-tablets. The dosage form can be of any shape suitable for oral administration of a drug, such as spheroidal, cube-shaped oval, or ellipsoidal.

Pharmaceutical compositions and dosage forms described herein may further comprise at least one additional active ingredient other than baclofen, a derivative thereof, or a pharmaceutically acceptable salt thereof that may or may not have the same pharmaceutical effect. Such compounds may be included to treat, prevent, and/or manage the same condition being treated, prevented, and/or managed with baclofen, a derivative thereof, or a pharmaceutically acceptable salt thereof, or a different one. Alternatively, such additional pharmaceutical compounds may be provided in a separate formulation and co-administered to a subject or patient with the baclofen, a derivative thereof, or a pharmaceutically acceptable salt thereof composition according to the present disclosure. Such separate formulations may be administered before, after, or simultaneously with the administration of baclofen, a derivative thereof or a pharmaceutically acceptable salt thereof compositions.

The compositions described above can be used in methods for treating, preventing, and/or managing various diseases and/or conditions, comprising administering to a subject or patient in need thereof a therapeutically effective amount of the active ingredient, a derivative thereof, or a pharmaceutically acceptable salt thereof.

The phrase "therapeutically effective amount" refers to the amount of the active ingredient, derivative thereof, or a pharmaceutically acceptable salt thereof, which alone or in combination with one or more other active ingredients, provides any therapeutic benefit in the prevention, treatment, and/or management of a particular diseases and/or condition.

Baclofen is a 4-amino-3-substituted-butanoic acid derivative and a structural analog of the inhibitory neurotransmitter gamma-aminobutyric acid (GABA), and may exert its effects by stimulation of the $GABA_B$ receptor subtype. Baclofen is a skeletal muscle relaxant and antispastic agent. Baclofen is useful for the alleviation of signs and symptoms of spasticity resulting from multiple sclerosis, particularly for the relief of flexor spasms and concomitant pain, clonus, and muscular rigidity. The inventors contemplate that a stabilized baclofen formulation according to the invention may be used for any indication for which baclofen is approved.

The amount of the dose of the active ingredient administered, as well as the dose frequency, will vary depending on the particular dosage form used and route of administration. The amount and frequency of administration will also vary according to the age, body weight, and response of the individual subject or patient. Typical dosing regimens can readily be determined by a competent physician without undue experimentation. It is also noted that the clinician or treating physician will know how and when to interrupt, adjust, or terminate therapy in conjunction with individual subject or patient response.

In general, the total daily dosage for treating, preventing, and/or managing the conditions associated with spasticity with any of the formulations according to the present disclosure is from about 1 mg to about 500 mg, or about 1, 5, 10, 15, 20, 25, 30, 35, 40, 45, 50, 55, 60, 70, 80, 90, 100, 120, 140, 150, 160, 180, 200, 250, 300, 350, 400, 450, or 500, mg, or any number in between, of baclofen, a derivative thereof, or a pharmaceutically acceptable salt thereof. Other indications may require higher doses, such as 600, 700, 800, 900, or even 1000 mg. For example, for an orally administered dosage form, the total daily dose may range from about 10 mg to about 100 mg, or from about 20 mg to about 90 mg, or from about 30 mg to about 80 mg, or from about 40 mg to about 70 mg. Accordingly, a single oral dose may be formulated to contain about 1, 5, 10, 15, 20, 25, 30, 35, 40, 45, 50, 55, 60, 70, 80, 90, 100, 120, 140, 150, 160, 180, or 200, mg, or any number in between, of baclofen, a derivative thereof or a pharmaceutically acceptable salt thereof. The pharmaceutical compositions containing baclofen, a derivative thereof or a pharmaceutically acceptable salt thereof may be administered in single or divided doses 1, 2, 3, 4, or more times each day. Alternatively, the dose may be delivered once every 2, 3, 4, 5, or more days. In one embodiment, the pharmaceutical compositions are administered once per day.

As used herein, the term "prevent" or "prevention" in the context of treatment, for example, as in "preventing spasticity" or "prevention of spasticity" refers to a reduction in the spasticity. Prevention does not require 100% elimination of the symptom.

EXAMPLES

The inventors assessed the stabilizing effects of poly (butylmethacrylate-co-(2-dimethylaminoethyl)methacrylate-co-methyl methacrylate (EUDRAGIT™ E PO, Evonik) on baclofen, gabapentin, and pregabalin in various compositions and manufacturing processes compared to the stabilizing effects of the α-amino acids used as stabilizers in U.S. Pat. No. 7,309,719.

Example 1—Accelerated Stability Studies

Baclofen formulations were prepared with pure API and a stabilizer selected from EUDRAGIT™ E PO ("PO" refers to powder; "EPO" used herein refers to EUDRAGIT™ E PO), glycine, L-leucine, and L-isoleucine in 1, 5, and 10% (m/m) concentrations or without any further ingredients, as provided in Table 1 below. Preparations were manufactured as:
dry powder blends treated in a mortar (T),
dry powder blends compacted in a tablet press punching tool ((K): 10 mm, round, no notch),
wet blends with ethanol (E), and
wet blends with water (W).

TABLE 1

| Test batch | Material | Amount [g] |
| --- | --- | --- |
| 1 | Baclofen | 60.000 |
| T/K/E/W | — | — |
| 2 | Baclofen | 59.400 |
| T/K/E/W | EUDRAGIT ™ E PO | 0.600 |
| 3 | Baclofen | 57.000 |
| T/K/E/W | EUDRAGIT ™ E PO | 3.000 |
| 4 | Baclofen | 54.000 |
| T/K/E/W | EUDRAGIT ™ E PO | 6.000 |
| 5 | Baclofen | 59.400 |
| T/K/E/W | Glycine | 0.600 |
| 6 | Baclofen | 57.000 |
| T/K/E/W | Glycine | 3.000 |
| 7 | Baclofen | 54.000 |
| T/K/E/W | Glycine | 6.000 |
| 8 | Baclofen | 59.400 |
| T/K/E/W | L-Leucine | 0.600 |
| 9 | Baclofen | 57.000 |
| T/K/E/W | L-Leucine | 3.000 |
| 10 | Baclofen | 54.000 |
| T/K/E/W | L-Leucine | 6.000 |
| 11 | Baclofen | 59.400 |
| T/K/E/W | L-Isoleucine | 0.600 |
| 12 | Baclofen | 57.000 |
| T/K/E/W | L-Isoleucine | 3.000 |
| 13 | Baclofen | 54.000 |
| T/K/E/W | L-Isoleucine | 6.000 |
| | Ethanol each E* | 4.000 |
| | Water purif. each W* | 4.000 |

Preparations were stored at 60° C. in closed glass vials. Samples were taken initially, after 1 week, and after 3 weeks. The samples were tested for impurity A (lactam) and unknown organic impurities by means of HPLC. The results are shown in FIGS. 1-4. (For baclofen, impurity A is 4-CPP.)

Gabapentin formulations and pregabalin formulations were also prepared with the same ratios of API to stabilizer described in Table 1 for baclofen. The preparations were stored in closed glass vials at 60° C. for gabapentin and at 80° C. for pregabalin. The content of lactam impurity A and unknown organic impurities for all three molecules was analyzed initially and after storage for defined periods by means of HPLC. These results are shown in FIGS. 5-12.

FIGS. 1-12 show that a stabilized and free-flowable pharmaceutical formulation can be obtained by several manufacturing processes, including dry compaction and wet granulation, of baclofen, gabapentin, and pregabalin with EUDRAGIT™ E. However, unexpectedly, only baclofen is stabilized by EUDRAGIT™ E.

Note that these experiments were performed with very large amounts of drug as compared to the stabilizer, so as to amplify the ability to observe lactam formation. Even though stabilization is observed at relatively low stabilizer: active ratios, the inventors contemplate using higher stabilizer:active ratios to maximize the stabilizing effect.

The accelerated stability data indicates that EUDRAGIT™ E stabilization is specific to baclofen alone. Based on the data gathered on the structurally similar molecules gabapentin and pregabalin, EUDRAGIT™ E was observed to have the opposite effect with formation of lactam impurity A being accelerated. In summary, EUDRAGIT™ E was observed to have a stabilization effect on baclofen and a destabilization effect on gabapentin and pregabalin.

Example 2—Infrared Spectroscopy to Assess Stabilization Mechanism on 4-Amino-3-Substituted-Butanoic Acid Derivatives by EUDRAGIT™ E To better elucidate the mechanistic understanding of EUDRAGIT™ E and the resultant stabilization effect with Baclofen, several mixtures were prepared as outlined below in Table 2. The % w/w concentration of EUDRAGIT™ E to Baclofen was altered to enable spectroscopic identification of any potential interaction.

TABLE 2

| Baclofen to EUDRAGIT™ E PO (% w/w) | Ratio EPO:Baclofen (w/w basis) |
|---|---|
| 10% | 9:1 |
| 15% | 5.7:1 |
| 20% | 4:1 |
| 40% | 1.5:1 |
| 60% | ~0.7:1 |

Figure 13:
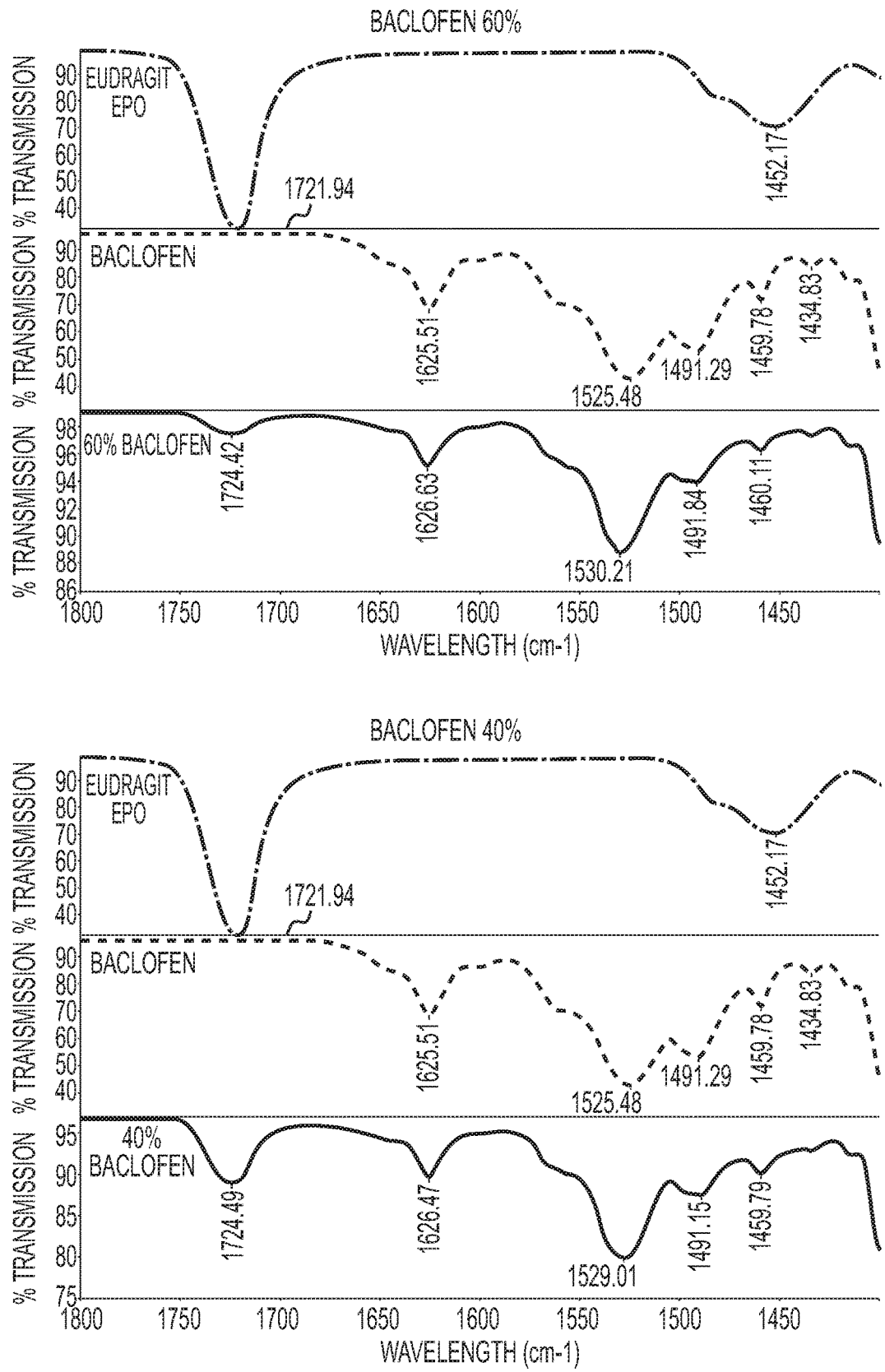
FIG. 13 shows IR spectra of 40:60 and 60:40 E PO/baclofen mixtures.
Figure 14:
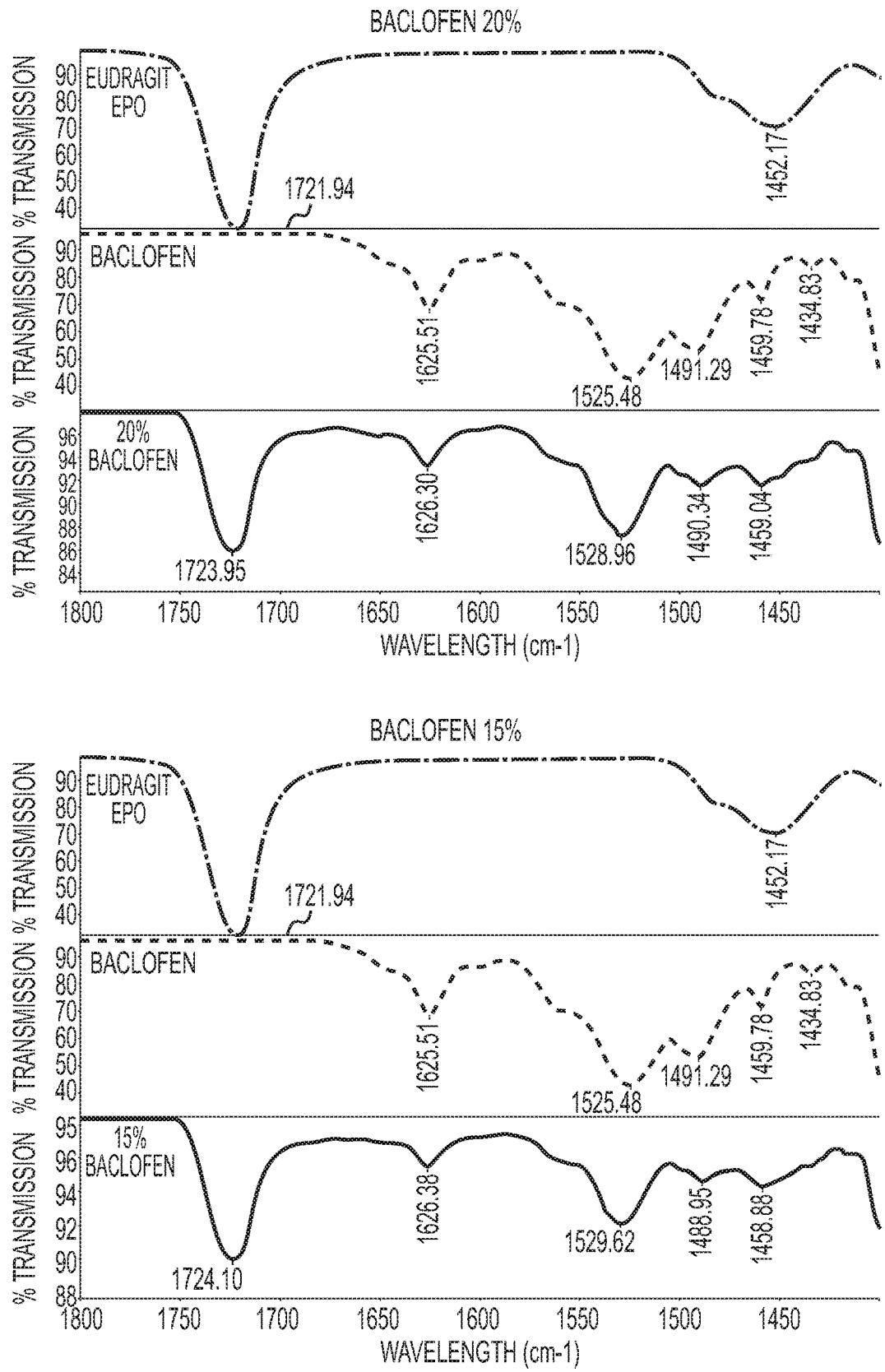
FIG. 14 shows IR spectra of 80:20 and 85:15 E PO/baclofen mixtures.

Infrared spectroscopy was performed on the mixtures outlined in Table 3 to assess any spectroscopic shift that occurred in comparison to EUDRAGIT™ E and Baclofen alone. The spectroscopic data shown in FIGS. 13-15 reveal that an EUDRAGIT™ E dependent shift of Baclofen (vibration C=O) from 1530 $cm^{-1}$ to 1525 $cm^{-1}$ and a lowered signal at 1490 $cm^{-1}$, which is indicative of a direct, stabilizing interaction of EPO amino group and the carboxylic group of baclofen. In contrast to baclofen, there was no observed EUDRAGIT™ E dependent shift in the 1400 to 1800 $cm^{-1}$ range of the spectrum, indicating that there was no direct interaction with EUDRAGIT™ E with gabapentin and pregabalin, as shown in FIG. 16.

Example 3—Formation of Baclofen Granules

Figure 17:
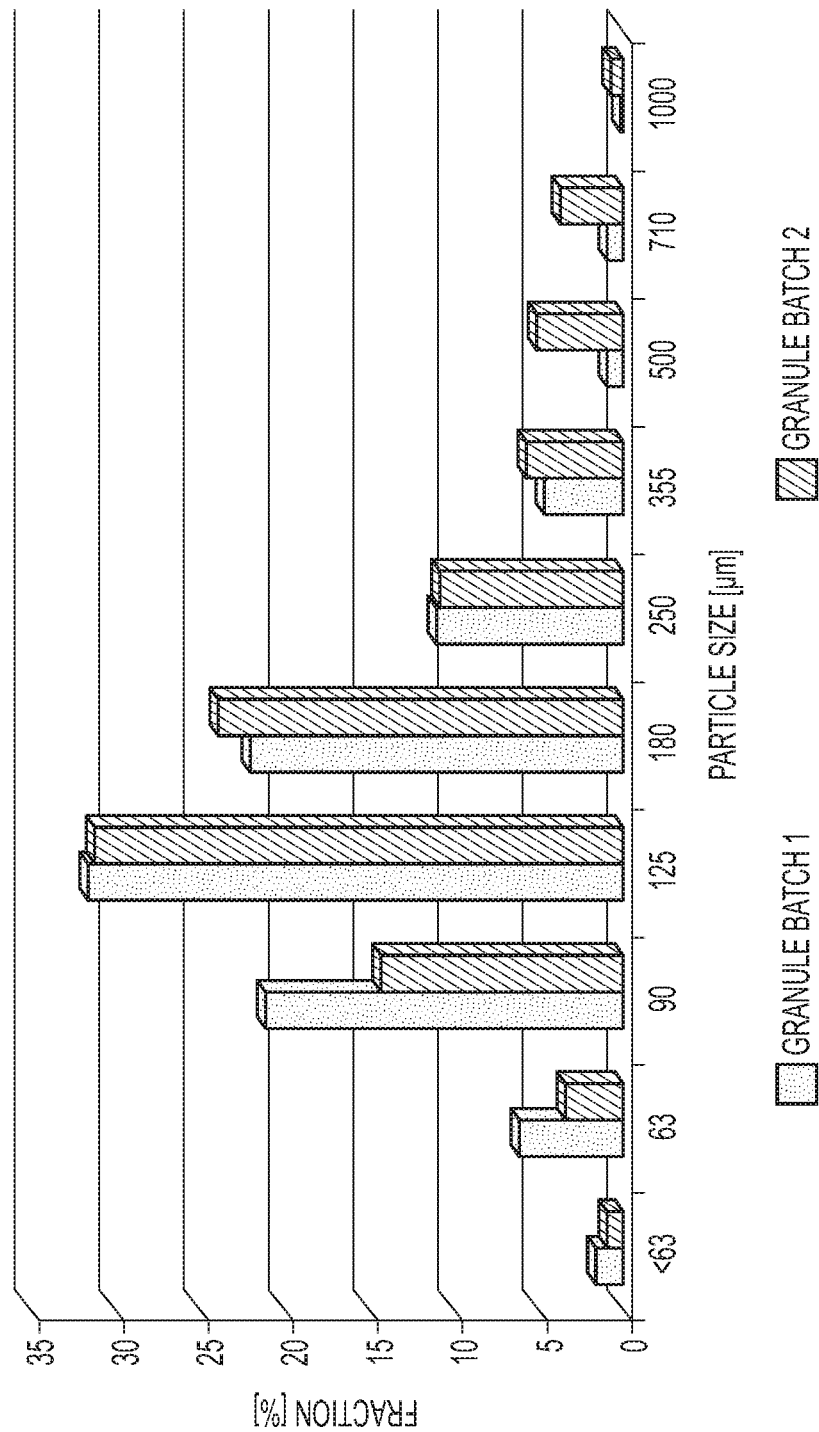
FIG. 17 shows particle size distribution by sieve analysis of two baclofen granule batches.

Granules were manufactured with a Zanchetta Roto P50 on a 8.79 kg scale (10.000 single doses). Baclofen and excipients were sieved through 1.0 mm, loaded into the granulator and dry blended for 10 min. Ethanol 96% was then sprayed onto the powder bed at a constant spraying pressure of 2 bar. Subsequently, the tip speed was increased and the wet mixture was massed for 10 min. The wet mixture was centered in the granulator and the granulator jacket was heated up to 60° C. The granules were dried under vacuum while tilting the granulator bowl and occasional stirring (every 500 sec for 10 sec at 80 rpm) for about 100 min. After discharging, the granules were dry sieved through 1.0 mm. Formula is summarized in Table 3. Particle size distribution by sieve analysis of the baclofen granule batches is shown in FIG. 17.

TABLE 3

| Single doses (SD) Material (Table 1 and Table 2) | Batch 1 10000 [mg/SD] | Batch 2 10000 [mg/SD] |
|---|---|---|
| Baclofen (micronized MCKO) | — | 20.00 |
| Mannitol | 332.00 | 332.00 |
| Xylitol | 420.00 | 400.00 |
| Saccharin sodium | 1.00 | 1.00 |
| Hypromellose | 60.00 | 60.00 |
| Amino Methacrylate Copolymer | 36.00 | 36.00 |
| Crospovidone | 30.00 | 30.00 |
| Alcohol (removed during operation) | 200.00 | 200.00 |
| Granules [mg/SD] | 879.00 | 879.00 |

Example 4—Formation of Final Blends

Figure 18:
FIG. 18 shows particle size distribution by sieve analysis of three baclofen final blends.

Placebo granules and API granules were processed to final blends. Colloidal silicon dioxide was sieved with a part of the placebo granules (or verum for the 20 mg formulation) through 1.0 mm. Strawberry flavor, calcium stearate, and talc were sieved separately (1.0 mm). Blending was performed via a Turbula mixer. Blending times and particularities are given in Table 4. FIG. 18 shows the particle size distribution by sieve analysis of the baclofen final blends.

TABLE 4

| Final blend batch | 1 | 2 | 3 |
|---|---|---|---|
| SD | 6000 | 5000 | 3000 |
| Dosage strength [mg/SD] | 5 | 10 | 20 |
| Material | [mg/SD] | [mg/SD] | [mg/SD] |
| Baclofen granules | 219.75 | 439.50 | 879.00 |
| Placebo granules | 659.25 | 439.50 | — |
| Colloidal silicon dioxide | 2.00 | 2.00 | 2.00 |
| Calcium stearate | 5.00 | 5.00 | 5.00 |
| Talc | 8.00 | 8.00 | 8.00 |
| Flavor strawberry | 6.00 | 6.00 | 6.00 |
| Final blend [mg/SD] | 900.00 | 900.00 | 900.00 |

Example 5—Filling of Stick Packs

Stick packs were filled with the previously manufactured final blends as described in Table 5, using a SBL-50 MERZ stick pack filling machine and a PET12/ALU9/PE50 43×80 mm stick pack foil. All blends were fillable with very low deviations of the filling mass given as standard deviation and maximum deviation. Baclofen content was uniform in all three batches as shown in Table 6.

TABLE 5

| Granules Final blend Stick packs | X | Y | Z |
|---|---|---|---|
| mg/SD | 5 | 10 | 20 |
| API grade | micronized | micronized | micronized |
| Stick pack foil | PET12/ALU9/PE50 43 × 80 mm | PET12/ALU9/PE50 43 × 80 mm | PET12/ALU9/PE50 43 × 80 mm |
| T (transversal sealing) [°C.] (left/right) | | 135/140 | |

TABLE 5-continued

| Granules Final blend Stick packs | X | Y | Z |
|---|---|---|---|
| T (longitudinal sealing) [°C.] (front/back) | | 130/130 | |
| Filling cycle [min$^{-1}$] | | 40 | |
| T (room) [° C.] | 20-21 | 20-21 | 21-22 |
| rH (room) [%] | 34-40 | 33-36 | 31 |
| Number of Sticks produced | 5000 | 4000 | 3500 |
| SD (max weight deviation) [%] | 0.5-1.2 (2.1) | 0.4-1.0 (2.0) | 0.4-0.6 (1.2) |

TABLE 6

| Granules Final blend Stick packs | X | Y | Z |
|---|---|---|---|
| mg/SD | 5 | 10 | 20 |
| API grade | micronized | micronized | micronized |
| X = | 98.521 | 98.035 | 98.568 |
| s = | 2.072 | 1.611 | 0.889 |
| AV = | 4.973 | 4.331 | 2.132 |

Example 6—Simulated Long-Term Stability Testing

Reliable estimates for ambient shelf-life values can be achieved in relatively short times by combining an experimental design that decouples temperature and relative humidity (RH) effects with an isoconversion paradigm[1]. The Accelerated Stability Assessment Program (ASAP) was conducted with two test batches P and Q having EPO: baclofen ratios of 3.6:1 (conditions described in Table 7).

[1] Waterman, AAPS PharmSciTech, Vol. 12, No. 3, 2011

TABLE 7

Study conditions and test schedule of ASAP

| Condition | Time Points | Storage Container |
|---|---|---|
| 50° C./75% RH | 4 d, 14 d | Open glass bottle stored in desiccators that is loaded with an aqueous NaCl slurry |
| 60° C./5% RH | 7 d, 14 d | Open glass bottle stored in desiccators that is loaded with an aqueous LiBr slurry |
| 60° C./45% RH | 4 d, 7 d | Open glass bottle stored in desiccators that is loaded with an aqueous $K_2CO_3$ slurry |
| 70° C./5% RH | 4 d, 14 d | Open glass bottle stored in desiccators that is loaded with an aqueous LiBr slurry |
| 70° C./75% RH | 8 h, 4 d | Open glass bottle stored in desiccators that is loaded with an aqueous NaCl slurry |
| 80° C./45% RH | 8 h, 24 h | Open glass bottle stored in desiccators that is loaded with an aqueous $K_2CO_3$ slurry |

Solid API and drug product chemical stability is affected by the RH that the sample experiences. The moisture modified Arrhenius equation (Equation 1) quantifies drug product stability as a function of temperature and humidity:
Equation 1: Moisture Modified Arrhenius Equation $$\ln k = \ln A - \frac{Ea}{RT} + B(RH)$$

where k is the degradation rate (typically percent degradant generated per day), A is the Arrhenius collision frequency, Ea is the energy of activation for the chemical reaction, R is the gas constant (1.986 cal/(mol K)), T is the temperature in Kelvin, and B is a humidity sensitivity constant which has been found to vary from 0 to 0.10. The form of Equation 1 indicates that chemical instability increases exponentially with an increase in RH. RH can have a very significant effect on chemical stability, depending on the B-term.

Using the modified Arrhenius equation the achieved data are evaluated and the terms k, Ea, and B are determined. For each temperature/relative humidity condition, the reaction rate k and the activation energy Ea are estimated from the slopes of the degradation rate (k) vs. time (t) line and ln(k) vs.1/T. The constant B is determined as the slope of the ln (k) vs. RH straight line.

Test batches P and Q were stressed as described in 7. Peak areas of Baclofen, 4-CPP, and the sum of all impurities before and after stressing are given as % for P (Table 8) and Q (Table 9). With the results at different time points, the degradation rates were calculated. Via Equation 1, rate constants (k) were calculated for different temperatures and relative humidities (Table 10). The shelf life at conditions for long term stability (25° C. and 60% RH) was predicted on the base of the mean activation energy (Ea) and a worst case scenario (Table 11). Even in the worst case, formation of 4% of 4-CPP (limit for Baclofen tablets in the USP) would need over 40 years. To ensure that even higher demands could be satisfied, the calculation was adapted for an acceptance value of 4-CPP at 0.5%, where a shelf life of 5.1 years was predicted in the worst case for batch P and 7.5 years for batch Q.

TABLE 8

Assay and purity of stored samples of batch P at different storage conditions and time points for ASAP

| Batch P | RT RRT | Baclofen 10.69 1.00 | 4-CPP 5.67 0.53 | sum of imp. | sum |
|---|---|---|---|---|---|
| 1 initial | | 99.93 | 0.00 | 0.07 | 100.00 |
| 2 initial | | 99.94 | 0.00 | 0.07 | 100.01 |
| 1 8 h@70° C./75% r.F | | 99.44 | 0.39 | 0.56 | 100.00 |
| 2 8 h@70° C./75% r.F | | 99.47 | 0.38 | 0.53 | 100.00 |
| 1 8 h@80° C./45% r.F | | 98.97 | 0.67 | 1.04 | 100.01 |
| 2 8 h@80° C./45% r.F | | 98.96 | 0.66 | 1.05 | 100.01 |
| 1 24 h@80° C./45% r.F | | 97.21 | 2.13 | 2.79 | 100.00 |
| 2 24 h@80° C./45% r.F | | 97.29 | 2.06 | 2.71 | 100.00 |
| 1 4 d@50° C./75% r.F | | 99.75 | 0.14 | 0.25 | 100.00 |
| 2 4 d@50° C./75% r.F | | 99.77 | 0.12 | 0.23 | 100.00 |
| 1 4 d@60° C./45% r.F | | 99.41 | 0.22 | 0.60 | 100.01 |
| 2 4 d@60° C./45% r.F | | 99.35 | 0.33 | 0.65 | 100.00 |
| 1 4 d@70° C./75% r.F | | 97.26 | 2.24 | 2.74 | 100.00 |
| 2 4 d@70° C./75% r.F | | 97.27 | 2.28 | 2.74 | 100.01 |
| 1 7 d@60° C./5% r.F | | 99.63 | 0.20 | 0.37 | 100.00 |
| 2 7 d@60° C./5% r.F | | 99.64 | 0.20 | 0.36 | 100.00 |
| 1 7 d@60° C./45% r.F | | 99.22 | 0.39 | 0.80 | 100.02 |
| 2 7 d@60° C./45% r.F | | 99.20 | 0.36 | 0.80 | 100.00 |
| 1 14 d@60° C./5% r.F | | 99.35 | 0.36 | 0.66 | 100.01 |
| 2 14 d@60° C./5% r.F | | 99.39 | 0.33 | 0.61 | 100.00 |
| 1 14 d@50° C./75% r.F | | 99.33 | 0.39 | 0.67 | 100.00 |
| 2 14 d@50° C./75% r.F | | 99.30 | 0.40 | 0.71 | 100.01 |

TABLE 8-continued

Assay and purity of stored samples of batch P at different storage conditions and time points for ASAP

| Batch P | RT RRT | Baclofen 10.69 1.00 | 4-CPP 5.67 0.53 | sum of imp. | sum |
|---|---|---|---|---|---|
| 1 14 d@70° C./5% r.F | | 98.03 | 1.59 | 1.98 | 100.01 |
| 2 14 d@70° C./5% r.F | | 98.05 | 1.56 | 1.94 | 99.99 |

TABLE 9

Assay and purity of stored samples of batch Q at different storage conditions and time points for ASAP

| Batch Q | RT RRT | Baclofen 10.69 1.00 | 4-CPP 5.67 0.53 | sum of imp. | sum |
|---|---|---|---|---|---|
| 1 initial | | 99.92 | 0.00 | 0.08 | 100.00 |
| 2 initial | | 99.93 | 0.00 | 0.07 | 100.00 |
| 1 8 h@70° C./75% r.F | | 99.71 | 0.23 | 0.30 | 100.01 |
| 2 8 h@70° C./75% r.F | | 99.70 | 0.23 | 0.30 | 100.00 |
| 1 8 h@80° C./45% r.F | | 99.47 | 0.43 | 0.53 | 100.00 |
| 2 8 h@80° C./45% r.F | | 99.47 | 0.42 | 0.53 | 100.00 |
| 1 24 h@80° C./45% r.F | | 98.06 | 1.45 | 1.95 | 100.01 |
| 2 24 h@80° C./45% r.F | | 98.02 | 1.49 | 1.98 | 100.00 |
| 1 4 d@50° C./75% r.F | | 99.76 | 0.09 | 0.25 | 100.01 |
| 2 4 d@50 °C./75% r.F | | 99.77 | 0.08 | 0.24 | 100.01 |
| 1 4 d@60 °C./45% r.F | | 99.69 | 0.14 | 0.31 | 100.00 |
| 2 4 d@60° C./45% r.F | | 99.74 | 0.14 | 0.25 | 99.99 |
| 1 4 d@70° C./75% r.F | | 98.10 | 1.44 | 1.90 | 100.00 |
| 2 4 d@70° C./75% r.F | | 98.09 | 1.52 | 1.92 | 100.01 |
| 1 7 d@60° C./5% r.F | | 99.78 | 0.12 | 0.22 | 100.00 |
| 2 7 d@60° C./5% r.F | | 99.77 | 0.13 | 0.23 | 100.00 |
| 1 7 d@60° C./45% r.F | | 99.63 | 0.27 | 0.37 | 100.00 |
| 2 7 d@60° C./45% r.F | | 99.66 | 0.26 | 0.35 | 100.01 |
| 1 14 d@60° C./5% r.F | | 99.48 | 0.28 | 0.53 | 100.01 |
| 2 14 d@60° C./5% r.F | | 99.45 | 0.30 | 0.57 | 100.02 |
| 1 14 d@50° C./75% r.F | | 99.50 | 0.23 | 0.49 | 99.99 |
| 2 14 d@50° C./75% r.F | | 99.49 | 0.27 | 0.50 | 99.99 |
| 1 14 d@70° C./5% r.F | | 97.86 | 1.84 | 2.15 | 100.01 |
| 2 14 d@70° C./5% r.F | | 97.71 | 1.98 | 2.30 | 100.01 |

TABLE 10

Rate constants (k) for 4-CPP formation at different temperatures and different RH

| Temperature [°C.] | 50 | 60 | 70 | 80 |
|---|---|---|---|---|
| Batch P | | | | |
| 5% RH | — | 0.02 | 0.11 | — |
| 45% RH | — | 0.05 | — | 2.09 |
| 75% RH | 0.03 | — | 0.54 | — |
| Batch Q | | | | |
| 5% RH | — | 0.02 | 0.14 | — |
| 45% RH | — | 0.04 | — | 1.47 |
| 75% RH | 0.02 | — | 0.36 | — |

TABLE 11

Predicted shelflife at 25° C. and 60% RH of batch P and batch Q with the mean calculated activation energy (Ea) and in the worst case

| | Batch P | | Batch Q | |
|---|---|---|---|---|
| Stability condition T[° C.]/RH[%] | Predicted shelf life 25/60 [Years] 4-CPP = 0.5% | 4-CPP = 4% | Predicted shelf life 25/60 [Years] 4-CPP = 0.5% | 4-CPP = 4 % |
| 50/75 (Mean Ea) | 8.5 | 67.8 | 17.5 | 139.9 |
| 50/75 (Worst case) | 5.1 | 40.8 | 7.5 | 60.2 |

Example 7: Real Long-Term Testing

To further demonstrate the effectiveness of the present invention in ensuring baclofen stability, six-month stability testing was performed under accelerated aging conditions (40° C., 75% RH).

TABLE 12

| Baclofen granules (5 mg) | | | | | | |
|---|---|---|---|---|---|---|
| Batch No.: X1 | Packaging material: PET 12/ALU 9/PE 50 stick pack foil (43 × 80 mm) | | | | | |
| | | | 40° C./75% rh | | | |
| Test | Period of storage Acceptance criteria | | Initial | 1 month Results | 3 months | 6 months |
| Content of baclofen by HPLC | 90.0-110.0% of nominal content | | 99.2% | 99.4% | 99.6% | 98.4% |
| Degradation products by HPLC | | | | | | |
| 4-CPP | n.m.t. 4.0% | | <0.05% | <0.05% | 0.06% | 0.13% |
| unknown impurity | n.m.t. 0.2% | | 0.06 % (RRT = 0.94) | <0.05% | <0.05% | <0.05% |
| total unknown impurities | n.m.t. 1.0% | | 0.06% | <0.05% | <0.05% | <0.05% |
| total of all impurities | n.m.t. 5.0% | | 0.06% | <0.05% | 0.06% | 0.13% |

TABLE 13

Baclofen granules (10 mg)

Batch No.: X2    Packaging material: PET 12/ALU 9/PE 50 stick pack foil (43 × 80 mm)
                                     40° C./75% rh

| Period of storage<br>Test | Acceptance criteria | Initial | 1 months | 3 months<br>Results | 6 months |
|---|---|---|---|---|---|
| Content of baclofen by HPLC | 90.0-110.0% of nominal content | 98.2% | 97.7% | 98.0% | 98.1% |
| Degradation products by HPLC | | | | | |
| 4-CPP | n.m.t. 4.0% | <0.05% | <0.05% | 0.06% | 0.14% |
| unknown impurity | n.m.t. 0.2% | <0.05% | <0.05% | <0.05% | 0.06% (RRT = 0.40) |
| total unknown impurities | n.m.t. 1.0% | <0.05% | <0.05% | <0.05% | 0.06% |
| total of all impurities | n.m.t. 5.0% | <0.05% | <0.05% | 0.06% | 0.20% |

TABLE 14

Baclofen granules (20 mg)

Batch No.: X3    Packaging material: PET 12/ALU 9/PE 50 stick pack foil (43 × 80 mm)
                                     40° C./75% rh

| Period of storage<br>Test | Acceptance criteria | Initial | 1 months | 3 months<br>Results | 6 months |
|---|---|---|---|---|---|
| Content of baclofen by HPLC | 90.0-110.0% of nominal content | 98.0% | 99.1% | 97.0% | 96.7% |
| Degradation products by HPLC | | | | | |
| 4-CPP | n.m.t. 4.0% | <0.05% | <0.05% | 0.07% | 0.14% |
| unknown impurity | n.m.t. 0.2% | <0.05% | 0.08 % (RRT = 0.67) | <0.05% | <0.05% |
| total unknown impurities | n.m.t. 1.0% | <0.05% | 0.08% | <0.05% | <0.05% |
| total of all impurities | n.m.t. 5.0% | <0.05% | 0.08% | 0.07% | 0.14% |

As can be seen from Tables 12-14 above, the stabilized baclofen formulations of the present invention have less than 0.2% of 4-CPP, even after six months of accelerated stability testing. That this stabilization occurred with baclofen, but not with related drugs gabapentin and pregabalin, is quite surprising. It is also commercially important and significant in that it solves a problem that has long existed with baclofen.

The present disclosure includes any combination of these various features or embodiments above and/or below as set forth in sentences and/or paragraphs. Any combination of disclosed features herein is considered part of the present disclosure and no limitation is intended with respect to combinable features.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

Other embodiments of the present disclosure will be apparent to those skilled in the art from consideration of the present specification and practice of the present disclosure disclosed herein. It is intended that the present specification and examples be considered as exemplary only with a true scope and spirit of the disclosure being indicated by the following claims and equivalents thereof.

What is claimed is:

1. An immediate release pharmaceutical composition, comprising an active ingredient selected from 4-amino-3-(4-chlorophenyl) butanoic acid) ("baclofen") and a pharmaceutically acceptable salt thereof; and a stabilizer, wherein the stabilizer is a copolymer of poly(butyl methacrylate-co-(2-dimethylaminoethyl) methacrylate-co-methyl methacrylate).

2. The immediate release composition of claim 1, wherein the active ingredient is dispersed throughout a matrix of the stabilizer.

3. The immediate release composition of claim 1, wherein the active ingredient and the stabilizer are intimately mixed in a-granular matrix composition.

4. The immediate release composition of claim 1, wherein a weight ratio of the stabilizer to the active ingredient is from about 1.5:1 to about 20:1.

5. The immediate release pharmaceutical composition of claim 1, further comprising one or more excipients selected from a group consisting of xylitol, calcium stearate, colloidal silicon dioxide, crospovidone, hypromellose, mannitol, saccharin sodium, talc, flavoring agent, and mixtures thereof.

6. An immediate release pharmaceutical composition, comprising an active ingredient selected from 4-amino-3-(4-chlorophenyl) butanoic acid) ("baclofen") and a pharmaceutically acceptable salt thereof and a stabilizer; wherein a weight ratio of the stabilizer to the active ingredient is from about 1.5:1 to about 20:1, and wherein the stabilizer is a copolymer of poly(butyl methacrylate-co-(2-dimethylaminoethyl) methacrylate-co-methyl methacrylate).

7. The immediate release composition of claim 6, wherein the active ingredient is dispersed throughout a matrix of the stabilizer.

8. The immediate release composition of claim 6, wherein the active ingredient and the stabilizer are intimately mixed in a granular matrix composition.

9. The immediate release pharmaceutical composition of claim 6, further comprising one or more excipients selected from a group consisting of xylitol, calcium stearate, colloidal silicon dioxide, crospovidone, hypromellose, mannitol, saccharin sodium, talc, flavoring agent, and mixtures thereof.

10. A method of making an immediate release pharmaceutical formulation comprising an active ingredient comprising 4-amino-3-(4-chlorophenyl) butanoic acid) ("baclofen") or a pharmaceutically acceptable salt thereof and a stabilizer; the method comprising intimately mixing the active ingredient and the stabilizer into a granular matrix blend;

wherein a weight ratio of the stabilizer to the active ingredient is from about 1.5:1 to about 20:1, and wherein the stabilizer is a copolymer of poly(butyl methacrylate-co-(2-dimethylaminoethyl) methacrylate-co-methyl methacrylate); and wherein the pharmaceutical formulation exhibits immediate release characteristics.

11. The method of claim 10, wherein the intimately mixing comprises at least one of wet granulation or dry granulation.

12. The method of claim 10, wherein the intimately mixing comprises dry blending of the active ingredient and the stabilizer to obtain a dry blend, followed by wet granulation of the dry blend.

13. The method of claim 12, wherein the wet granulation comprises wetting the dry blend with ethanol and wet mixing, drying, and cooling to obtain granules comprising the active ingredient and the stabilizer.

\* \* \* \* \*